United States Patent [19]

Lee et al.

[11] Patent Number: 5,489,611
[45] Date of Patent: Feb. 6, 1996

[54] METHOD FOR LOWERING PLASMA LEVELS OF LIPOPROTEIN (A)

[75] Inventors: Helen T. Lee, Ann Arbor; Joseph A. Picard, Canton; Randy R. Ramharack; Bruce D. Roth, both of Ann Arbor; Drago R. Sliskovic, Saline, all of Mich.

[73] Assignee: Warner-Lambert Company, Morris Plains, N.J.

[21] Appl. No.: 388,043

[22] Filed: Feb. 10, 1995

[51] Int. Cl.$^6$ .......................... A61K 31/19; A61K 31/11; A61K 31/07

[52] U.S. Cl. .......................... 514/557; 514/703; 514/725; 514/824

[58] Field of Search .................................... 514/557, 703, 514/725, 824

[56] References Cited

U.S. PATENT DOCUMENTS 5,219,888  6/1993  Katocs, Jr. et al. .................... 514/560

OTHER PUBLICATIONS

*Am. J. Clin. Nutr.*, vol. 53, 1991, Ringer et al., pp. 688–694.
*Retinoids: New Trends in Research and Therapy*, Retinoid Symp., Geneva 1984, Gollnick et al., pp. 445–460.
*British Journal of Dermatology*, vol. 107, 1982, Lyons et al., pp. 591–595.
*Advanced in Drug Research*, vol. 24, 1993, Shudo et al., pp. 81–119.

*Primary Examiner*—Kimberly Jordan
*Attorney, Agent, or Firm*—Charles W. Ashbrook

[57] ABSTRACT

Retinoids are effective to lower plasma levels of Lp (a) in mammals.

11 Claims, No Drawings

1

METHOD FOR LOWERING PLASMA LEVELS OF LIPOPROTEIN (A)

FIELD OF THE INVENTION

This invention relates to a method for lowering plasma levels of a lipoprotein known as lipoprotein(a), Lp(a), in animals comprising administering a retinoid compound.

BACKGROUND OF THE INVENTION

Heart disease remains one of the leading causes of death. The high incidence of heart disease has led to the identification of various risk factors that may be controlled in an effort to reduce such disease. One risk factor is hypercholesterolemia, which is a condition of high blood levels of cholesterol. Cholesterol is a fatty substance that is made by the liver, and also is present in many foods. Cholesterol circulates in the blood associated with several forms of lipoproteins. Some of these forms are now referred to as "good" forms of cholesterol, while others are "bad". For example, one such lipoprotein with which cholesterol associates is referred to as low-density lipoprotein or LDL. LDL-cholesterol (LCL-C) is the form in which cholesterol leaves the liver destined for cells throughout the body. High levels of LDL-C are bad, because they have been shown to cause rapid clogging of coronary arteries with fatty deposits, resulting in the disease known as atherosclerosis, which often leads to heart attacks. A great deal of effort is currently underway to get people to reduce their levels of LDL-C, for example, by modifying diet and exercise.

In contrast, a good form of cholesterol is that associated with high-density lipoprotein, ie, HDL-cholesterol (HDL-C). This is the form in which cholesterol is pulled out of cells and goes back to the liver for disposal.

A modified form of LDL is known as lipoprotein(a), "Lp(a)". It consists of LDL covalently linked through a disulfide bond to apolipoprotein(a), "apo(a)". Lp(a) cholesterol appears to be a bad form of cholesterol, since elevated levels of Lp(a) have been associated with the development of atherosclerosis, coronary heart disease, myocardial infarction, cerebral infarction, and restenosis following balloon angioplasty. In fact, Lp(a) appears to be an excellent predictor for stroke. Accordingly, high concentrations of Lp(a) is one of the major risk factors leading to death from heart disease.

We have now discovered that retinoids are effective in lowering plasma concentrations of Lp(a). This invention thus provides a method for lowering plasma levels of Lp(a) comprising administering a retinoid.

Retinoids are a class of natural and synthetic organic molecules which modulate the activity of retinoid responsive genes, mRNAs, and proteins. Some activities of retinoids occur by interaction with families of nuclear receptors, including the retinoic acid receptors and the retinoid X receptors. Vitamin A is a natural retinoid known as retinol. "Vitamin A acid" is retinoic acid. Retinoids have been reported to have a number of biological activities. For example, they are said to be potent agents for control of both cellular differentiation and proliferation. They have been reported to moderate the growth of tumors and to affect the immune system, see Gale, *Progress in Medicinal Chem.* 1993;30, Ellis and Luscombe ed., Elsevier Publishers.

Retinoids have also been reported to have effects on plasma concentrations of lipoproteins. For example, Lyons, et al., *Br. J. Dermatology* 1982;107:591–5, reported a decrease in HDL-C levels in patients given 13-cis-retinoic acid. Ringer, et al., *Am. J. Chem. Nutr.* 1991;53:688–94, reported an increase in HDL concentrations in patients given β-carotene, but did not find any changes in apolipoprotein A or B levels. Katocs, et al., U.S. Pat. No. 5,219,888, reported that retinoids increase plasma HDL levels.

There have been no reports that retinoids effect plasma levels of Lp(a). We have now discovered that plasma Lp(a) can be lowered by administering retinoids, and accordingly an object of this invention is to provide a method for lowering Lp(a), and thereby treating and preventing coronary artery disease.

SUMMARY OF THE INVENTION

This invention provides a method for lowering plasma levels of Lp(a) using a retinoid. More particularly, the invention is a method for lowering plasma levels of Lp(a) in animals comprising administering to an animal an Lp(a) lowering amount of a retinoid. By lowering Lp(a) levels, the animals are protected against developing premature atherosclerosis and consequent coronary artery disease.

Numerous compounds are known which are characterized as retinoids. A comprehensive discussion of retinoids is given by Dawson and Hobbs, in Chapter 2 of *The Retinoids: Biology, Chemistry, and Medicine,* 2nd ed., Sporn, Roberts, and Goodman, Raven Press, Ltd., New York, 1994. That reference is incorporated herein by reference for its teaching of the synthesis of retinoids. All that is required by this invention is that a compound characterized as a retinoid is administered to an animal in an Lp(a) lowering amount.

Preferred retinoids to be utilized in the present invention include retinoic acid of the formula

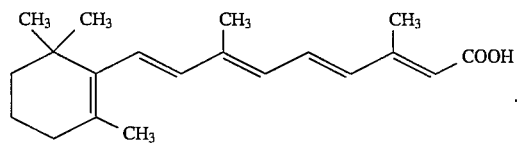

Retinoic acid derivatives also are preferred, for example compounds of the formula

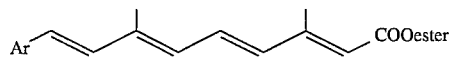

wherein Ar is an aryl group and "ester" is an organic ester forming group.

Retinoids which are dienyl benzoic acid and enzynylaryl carboxylic acids also are preferred. For example, compounds of the formula

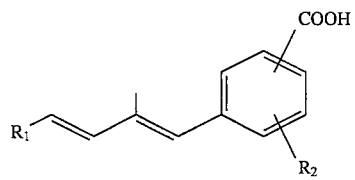

where $R_1$ is cycloalkyl or aryl, and $R_2$ is a typical phenyl substituted group such as halo, alkyl, alkoxy, alkylthio, and the like.

Compounds such as

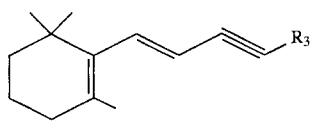

where $R_3$ is, for instance

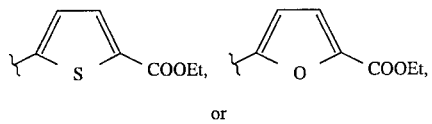

or

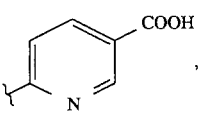

also are preferred.

All of the retinoids required for this invention are known and available by well-known synthetic methodologies.

A further embodiment of this invention is a method for identifying animals who are likely to encounter a stroke. Such animals have a higher than normal plasma level of Lp(a). The method comprising determining plasma level of Lp(a) and comparing it to levels that are normal for the particular age and sex group to which the subject belongs.

DETAILED DESCRIPTION OF THE INVENTION

All that is required for this invention is to administer an Lp(a) lowering amount of a retinoid to an animal in order to diminish plasma levels of Lp(a).

Preferred retinoids to be utilized are benzoic acids and carboxylic acids and esters thereof, particularly $C_1$–$C_6$ alkyl esters, such as methyl, ethyl, isopropyl, isopentyl, and n-hexyl.

Typical benzoic acids to be utilized include those of the formula

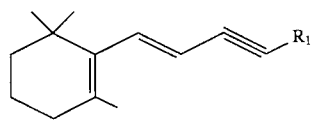

wherein $R_1$ is cycloalkyl or aryl and $R_2'$ independently are:
$R_2$ substituent group such as halo, hydroxy, amine, mono- and dialkyl amino, $C_1$–$C_6$ alkyl, $C_1$–$C_6$ alkoxy, or $C_1$–$C_6$ alkylthio, and n is 0 or 1. The cycloalkyl group can be a single ring, for instance a $C_3$–$C_7$ cycloalkyl ring, optionally substituted with halo, alkyl, alkoxy, alkylthio, or the like, or bicyclic. Similarly, the aryl can be monocyclic or bicyclic, for instance, phenyl or naphthyl, it can be cycloalkyl fused to an aromatic ring, for instance, a benzocyclohexane or benzocycloheptane, and any of the ring systems can contain heteroatoms, for instance, 1, 2, or 3 heteroatoms selected from sulfur, oxygen, and nitrogen. The rings can also be substituted, for example, with 1, 2, or 3 groups such as $R_2$ and $R_2'$. Many of the retinoids have an alkylene chain which can exist as cis and trans isomers. Both the all cis and all trans, as well as mixtures, can be used herein.

Examples of preferred retinoids to be utilized in the method of this invention include those having the following structures:

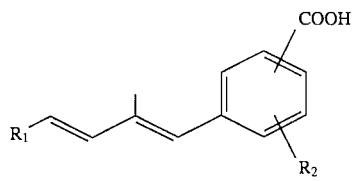

where $R_1$ is, for instance

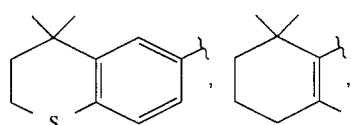

and

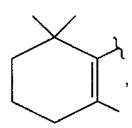

and $R_2$ is hydrogen, halo, or alkoxy;

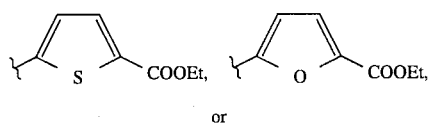

where $R_1$ is

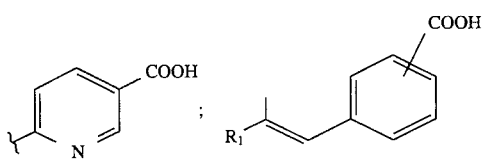

or

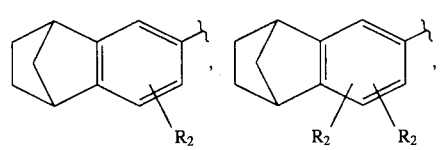

where $R_1$ is alkyl or dialkylphenyl, or a bi- or tricyclic ring such as:

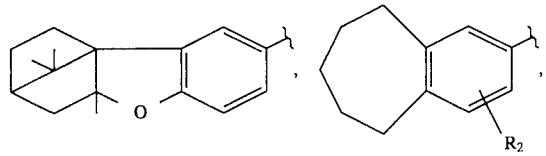

The typical specific retinoids which can be utilized in the method of the invention include the following:

4-[4-(4,4-Dimethyl-thiochroman-6-oyl)-2-methyl-buta-1,3-dienyl]-benzoic acid;

3-Fluoro-4-[2-methyl-4-(2,6,6-trimethyl-cyclohex-1-enyl)-buta-1,3-dienyl]-benzoic acid;

3-Methoxy-4-[2-methyl-4-(2,6,6-trimethyl-cyclohex-1-enyl)-buta-1,3-dienyl]-benzoic acid;

5-[4-(2,6,6-Trimethyl-cyclohex-1-enyl)-but-3-en-1-ynyl]-thiophene-2-carboxylic acid ethyl ester;

5-[4-(2,6,6-Trimethyl-cyclohex-1-enyl)-but-3-en-1-ynyl]-furan-2-carboxylic acid ethyl ester;

6-[4-(2,6,6-Trimethyl-cyclohex-1-enyl)-but-3-en-1-ynyl]-nicotinic acid;

4-[2-(3-tert-Butyl-phenyl)-propenyl]-benzoic acid;

4-[2-(4-tert-Butyl-phenyl)-propenyl]-benzoic acid;

4-[2-(3,4-Dimethyl-phenyl)-propenyl]-benzoic acid;

4-[2-(3,4-Diethyl-phenyl)-propenyl]-benzoic acid;

4-[2-(3,4-Diisopropyl-phenyl)-propenyl]-benzoic acid;

4-[2-(5-Isobutyl-tricyclo[6.2.1.0>2,7]undeca-2,4,6-trien-4-yl)-propenyl]-benzoic acid;

4-[2-(3,6-Dimethoxy-tricyclo[6.2.1.0>2,7]undeca-2,4,6-trien-4-yl)-propenyl]-benzoic acid;

Benzoic acid, 4-[2-(2,3,4,4a-tetrahydro-4a,10,10-trimethyl-1H-3,9b-methanodibenzofuran-8-yl)ethenyl]-;

4-[2-(6,7,8,9-Tetrahydro-5H-benzocyclohepten-2-yl)propenyl]-benzoic acid;

4-[2-(7-Methyl-6,7,8,9-tetrahydro-5H-benzocyclohepten-2-yl)-propenyl]-benzoic acid ethyl ester;

4-[2-(5,5-Dimethyl-6,7,8,9-tetrahydro-5H-benzocyclohepten-2-yl)-propenyl]-benzoic acid ethyl ester;

4-[2-(3,7,7-Trimethyl-6,7,8,9-tetrahydro-5H-benzocyclohepten-2-yl)-propenyl]-benzoic acid methyl ester;

4-[2-(7,7-Dimethyl-3-octyl-6,7,8,9-tetrahydro-5H-benzocyclohepten-2-yl)-propenyl]-benzoic acid;

4-[2-(7-Ethyl-7-methyl-6,7,8,9-tetrahydro-5H-benzocyclohepten-2-yl)-propenyl]-benzoic acid ethyl ester;

Benzoic acid, 4-[2-(5,6,8,9-tetrahydro-spiro[7H-benzocycloheptene-7,1'-cyclopropane]-2-yl)-1-propenyl]-, ethyl ester;

Benzoic acid, 4-[2-(5,6,8,9-tetrahydro-spiro-[7H-benzocycloheptene-7,1'-cyclopentane]-2-yl)-1-propenyl]-, ethyl ester;

4-[2-(7-Oxo-6,7,8,9-tetrahydro-5H-benzocyclohepten-2-yl)-propenyl]-benzoic acid ethyl ester;

4-[2-(9-Methyl-6,7,8,9-tetrahydro-5H-benzocyclohepten-2-yl)-propenyl]-benzoic acid ethyl ester;

4-[2-(5,5,9-Trimethyl-6,7,8,9-tetrahydro-5H-benzocyclohepten-2-yl)-propenyl]-benzoic acid ethyl ester;

4-[2-(7,7,9-Trimethyl-6,7,8,9-tetrahydro-5H-benzocyclohepten-2-yl)-propenyl]-benzoic acid ethyl ester;

4-[2-(5,9,9-Trimethyl-6,7,8,9-tetrahydro-5H-benzocyclohepten-2-yl)-propenyl]-benzoic acid ethyl ester;

4-[2-(7,7,9,9-Tetramethyl-6,7,8,9-tetrahydro-5H-benzocyclohepten-2-yl)-propenyl]-benzoic acid;

4-[2-(6,6,8,8-Tetramethyl-7-oxo-6,7,8,9-tetrahydro-5H-benzocyclohepten-2-yl)-propenyl]-benzoic acid ethyl ester;

4-[2-(4,4-Dimethyl-chroman-7-yl)-propenyl]-benzoic acid;

4-[2-(4,4-Dimethyl-1,1-dioxo-thiochroman-7-yl)-propenyl]-benzoic acid;

4-[2-(1,4,4-Trimethyl-1,2,3,4-tetrahydro-quinolin-7-yl)-propenyl]-benzoic acid;

4-[2-(2,3-Dihydro-benzo[1,4]dioxin-6-yl)-propenyl]-benzoic acid;

4-[2-(2,3-Dihydro-benzo[1,4]dithiin-6-yl)-propenyl]-benzoic acid;

4-[2-(1,4-Dimethyl-1,2,3,4-tetrahydro-quinoxalin-6-yl)-propenyl]-benzoic acid;

4-[2-(2,3,4,5-Tetrahydro-benzo[b]oxepin-8-yl)-propenyl]-benzoic acid;

4-[2-(2,3,4,5-Tetrahydro-benzo[b]oxepin-7-yl)-propenyl]-benzoic acid;

4-[2-(2,3,4,5-Tetrahydro-benzo[b]thiepin-8-yl) propenyl]-benzoic acid;

4-[2-(5-Methyl-2,3,4,5-tetrahydro-benzo[b]thiepin-8-yl)-propenyl]-benzoic acid;

4-[2-(5,5-Dimethyl-2,3,4,5-tetrahydro-benzo[b]thiepin-8-yl)-propenyl]-benzoic acid;

4-[2-(3,3-Dimethyl-2,3,4,5-tetrahydro-benzo[b]thiepin-8-yl)-propenyl]-benzoic acid;

4-[2-(2,3,4,5-Tetrahydro-benzo[b]thiepin-7-yl)-propenyl]-benzoic acid;

4-[2-(5-Methyl-2,3,4,5-tetrahydro-benzo[b]thiepin-7-yl)-propenyl]-benzoic acid;

4-[2-(3-Methyl-2,3,4,5-tetrahydro-benzo[b]thiepin-7-yl)-propenyl]-benzoic acid;

4-[2-(3,5,5-Trimethyl-2,3,4,5-tetrahydro-benzo[b]thiepin-7-yl)-propenyl]-benzoic acid;

4-[2-(3,3-Dimethyl-2,3,4,5-tetrahydro-benzo [b]thiepin-7-yl)-propenyl]-benzoic acid;

4-[2-(1,1-Dioxo-2,3,4,5-tetrahydro-benzo[b]thiepin-8-yl)-propenyl]-benzoic acid;

4-[2-(1,1-Dioxo-2,3,4,5-tetrahydro-benzo[b]thiepin-7-yl)-propenyl]-benzoic acid;

4-[2-(5,5-Dimethyl-1,1-dioxo-2,3,4,5-tetrahydro-benzo [b]thiepin- 7-yl)-propenyl]-benzoic acid;

4-[2-(3-Methyl-1,1-dioxo-2,3,4,5-tetrahydro-benzo[b] thiepin- 7-yl)-propenyl]-benzoic acid;

4-[2-(3,4-Dihydro-2H-benzo[b][1,4]dioxepin-7-yl)-propenyl]benzoic acid;

4-[2-(3-Methyl-3,4-dihydro-2H-benzo [b][1,4]-dioxepin-7-yl)-propenyl]-benzoic acid;

4-[2-(7,7-Dimethyl-7,8-dihydro-6H-5-oxa-9-thiabenzocyclohepten- 2-yl)-propenyl]-benzoic acid;

4-[2-(7,8-Dihydro-6H-5,9-dithia-benzocyclohepten-2-yl)-propenyl]-benzoic acid;

4-[2-(7-Methyl-7,8-dihydro-6H-5,9-dithia-benzocyclohepten- 2-yl)-propenyl]-benzoic acid;

4-[2-(5-Methyl-2,3,4,5-tetrahydro-benzo[b][ 1,4]thiazepin-8-yl)-propenyl]-benzoic acid;

4-[2-(3,5-Dimethyl-2,3,4,5-tetrahydro-benzo[b][ 1,4]thiazepin-8-yl)-propenyl]-benzoic acid;

4-[2-(2,2-Dimethyl-benzo[1,3]dioxol-5-yl)-propenyl]-benzoic acid;

4-[2-(2,2-Dimethyl-benzo[1,3]dithiol-5-yl)-propenyl]-benzoic acid;

4-Styryl-benzoic acid;

4-[2-(4-tert-Butyl-phenyl)-vinyl]-benzoic acid;

4-(2-Tricyclo[6.2.1.0>2,7_]undeca-2,4,6-trien-4-yl-vinyl)-benzoic acid;

Benzoic acid, 4-[2-(2,3,4,4a-tetrahydro-4a, 10,10-trimethyl-1H-3,9b-methanodibenzofuran-8-yl)-ethenyl]-;

4-[2-(4-Methoxy-2,3,6-trimethyl-phenyl)-vinyl]benzoic acid;

4-{2-[4-(3-Methyl-but-2-enyloxy)-phenyl]-vinyl}-benzoic acid ethyl ester;

4-{2-[2-Methyl-4-(3-methyl-but-2-enyloxy)-phenyl[-vinyl}-benzoic acid ethyl ester;

4-{2-[2-Methyl-4-(3-methyl-but-2-enylsulfanyl)-phenyl]-vinyl}-benzoic acid ethyl ester;

4-[2-(5,5,8,8-Tetramethyl-5,6,7,8-tetrahydro-naphthalen-2-yl)-vinyl]-benzoic acid;

4-[2-(1-Methoxy-4,5,5,8,8-pentamethyl-5,6,7,8-tetrahydro-naphthalen-2-yl)-vinyl]-benzoic acid;

4-[2-(1-Methoxy-3,5,5,8,8-pentamethyl-5,6,7,8-tetrahydro-naphthalen-2-yl)-vinyl]-benzoic acid;

4-[2-(1,4-Dimethoxy-5,5,8,8-tetramethyl-5,6,7,8-tetrahydro-naphthalen-2-yl)-vinyl]-benzoic acid;

4-[2-(1,3-Dimethoxy-5,5,8,8-tetramethyl-5,6,7,8-tetrahydro-naphthalen-2-yl)-vinyl]-benzoic acid;

4-[2-(1-Ethoxy-3-methoxy-5,5,8,8-tetramethyl-5,6,7,8-tetrahydro-naphthalen-2-yl)-vinyl]-benzoic acid;

4-[2-(1-Isopropoxy-3-methoxy-5,5,8,8-tetramethyl-5,6,7,8-tetrahydro-naphthalen-2-yl)-vinyl]-benzoic acid;

4-[2-(3-Methoxy-5,5,8,8-tetramethyl-1-propoxy-5,6,7,8-tetrahydro-naphthalen-2-yl)-vinyl]-benzoic acid;

4-[2-(1-Butoxy-3-methoxy-5,5,8,8-tetramethyl-5,6,7,8-tetrahydro-naphthalen-2-yl)-vinyl]-benzoic acid;

4-[2-(1-Hexyloxy-3-methoxy-5,5,8,8-tetramethyl-5,6,7,8-tetrahydro-naphthalen-2-yl)-vinyl]-benzoic acid;

4-(1,1,3,3-Tetramethyl-indan-5-ylethynyl)-benzoic acid;

4-(1,1,2,3,3-Pentamethyl-indan-5-ylethynyl)-benzoic acid;

4-(3,8,8-Trimethyl-5,6,7,8-tetrahydro-naphthalen-2-ylethynyl)-benzoic acid;

4-(3-Methoxy-5,5,8,8-tetramethyl-5,6,7,8-tetrahydro-naphthalen- 2-ylethynyl)-benzoic acid;

6-(4,4,7-Trimethyl-chroman-6-ylethynyl)-nicotinic acid ethyl ester;

6-(3,3,4,4-Tetramethyl-chroman-6-ylethynyl)-nicotinic acid ethyl ester;

6-(3,3,4,4,7-Pentamethyl-chroman-6-ylethynyl)-nicotinic acid ethyl ester;

6-(4,4-Dimethyl-thiochroman-6-ylethynyl)-nicotinic acid ethyl ester;

6-(4,4,7-Trimethyl-thiochroman-6-ylethynyl)-nicotinic acid ethyl ester;

4-[5-(1,1,2,3,3-Pentamethyl-indan-5-yl)-1H-pyrazol-3-yl]-benzoic acid methyl ester;

4-[5-(3-Methyl-5,6,7,8-tetrahydro-naphthalen-2-yl)-1H-pyrazol-3-yl]-benzoic acid methyl ester;

4-[3-(5,5,8,8-Tetramethyl-5,6,7,8-tetrahydro-naphthalen-2-yl)-pyrazol-1-yl]-benzoic acid;

4-[2-(5,5,8,8-Tetramethyl-5,6,7,8-tetrahydro-naphthalen-2-yl)-1H-imidazol-4-yl]-benzoic acid ethyl ester;

4-[5-(5,5,8,8-Tetramethyl-5,6,7,8-tetrahydro-naphthalen-2-yl)-1H-imidazol-2-yl]-benzoic acid methyl ester;

4-[5-Oxo-3-(5,5,8,8-tetramethyl-5,6,7,8-tetrahydro-naphthalen- 2-yl)-4,5-dihydro-pyrazol-1-yl]benzoic acid;

4-[2-Mercapto-4-(5,5,8,8-tetramethyl-5,6,7,8-tetrahydro-naphthalen-2-yl)-imidazol-1-yl]-benzoic acid;

4-[4-(5,5,8,8-Tetramethyl-5,6,7,8-tetrahydro-naphthalen-2-yl)-oxazol-2-yl]-benzoic acid methyl ester;

4-[5-(5,5,8,8-Tetramethyl-5,6,7,8-tetrahydro-naphthalen-2-yl)-oxazol-2-yl]-benzoic acid methyl ester;

4-[5-(5,5,8,8-Tetramethyl-5,6,7,8-tetrahydro-naphthalen-2-yl)-oxazolidin-3-yl]-benzoic acid ethyl ester;

4-[3-(7-Hydroxy-5,5,8,8-tetramethyl- 5,6,7,8-tetrahydro-naphthalen-2-yl)-isoxazol-5-yl]benzoic acid;

4-[4-(5,5,8,8-Tetramethyl-5,6,7,8-tetrahydro-naphthalen-2-yl)-thiazol -2-yl]-benzoic acid methyl ester;

4-[3-(5,5,8,8-Tetramethyl-5,6,7,8-tetrahydro-naphthalen-2-yl)-[1,2,4 ]oxadiazol-5-yl]-benzoic acid methyl ester;

4-[6-(5,5,8,8-Tetramethyl-5,6,7,8-tetrahydro-naphthalen-2-yl)-pyridazin-4-yl]-benzoic acid methyl ester;

4-[6-(5,5,8,8-Tetramethyl-5,6,7,8-tetrahydro-naphthalen-2-yl)-pyridazin-3-yl]-benzoic acid methyl ester;

4-[2-Hydroxy-6-(5,5,8,8-tetramethyl-5,6,7,8-tetrahydro-naphthalen-2-yl)-pyrimidin-4-yl]-benzoic acid butyl ester;

6-m-Tolyl-naphthalene-2-carboxylic acid;

6-(3-tert -Butyl-phenyl)-naphthalene-2-carboxylic acid;

6-(3-tert-Butyl-4-methoxy-phenyl)-naphthalene-2-carboxylic acid;

6-(3-Adamantan-1-yl-4-methoxy-phenyl)-naphthalene-2-carboxylic acid;

6-(3-Adamantan-1-yl-4-hexyloxy-phenyl)-naphthalene-2-carboxylic acid;

6-(3-Adamantan-1-yl-4-decyloxy-phenyl)-naphthalene-2-carboxylic acid;

2-Naphthalenecarboxylic acid, 6-(2,3,4,4a-tetrahydro-4a,10,10-trimethyl-1H-3,9b-methanodibenzofuran-8-yl)-;

6-[4-(Methoxy-3-(1-methyl-1-nonyloxy-ethyl)-phenyl]-naphthalene-2-carboxylic acid;

6-(3,4-Dimethoxy-phenyl)-naphthalene-2-carboxylic acid;

6-[4-(Adamantan-1-ylsulfanyl)-phenyl]-naphthalene-2-carboxylic acid;

8-Methoxy-5',5',8',8'-tetramethyl- 5',6',7',8'-tetrahydro-[2,2']binaphthalenyl-6-carboxylic acid;

6-(3-Adamantan-1-yl-4-methoxy -phenyl)-4-hydroxy-1-methyl-naphthalene-2-carboxylic acid;

2-(4-tert -Butyl-phenyl)-benzofuran-6-carboxylic acid;

2-(4-tert-Butyl-phenyl)-benzo[b]thiophene- 6-carboxylic acid;

2-(4-tert-Butyl-phenyl)-1H-indole-6-carboxylic acid;

2-(3-tert-Butyl-4-methoxy-phenyl)-benzofuran- 6-carboxylic acid;

2-(5,5,8,8-Tetramethyl-5,6,7,8-tetrahydro-naphthalen-2-yl)-benzofuran-6-carboxylic acid;

2-(5,5,8,8-Tetramethyl-5,6,7,8-tetrahydro-naphthalen-2-yl)-benzooxazole -6-carboxylic acid;

2-(5,5,8,8-Tetramethyl-5,6,7,8-tetrahydro-naphthalen-2-yl)-3H-benzoimidazole-5-carboxylic acid;

2-(3-Adamantan-1-yl-4-methoxy-phenyl)-benzofuran-6-carboxylic acid;

2-(3-Adamantan-1-yl-4-methoxy-phenyl)-benzo[b]thiophene-6-carboxylic acid;

2-(3-Adamantan-1-yl-4-methoxy-phenyl)-3H-benzo-imidazole-5-carboxylic acid;

2-(3-Adamantan-1-yl-4-hydroxy-phenyl)-3H-benzo-imidazole-5-carboxylic acid;

2-(3-Adamantan-1-yl-4-decyloxy-phenyl)-benzooxazole-6-carboxylic acid;

Benzo[b]thiophene-6-carboxylic acid, 2(2,3,4,4a-tetrahydro-4a,10,10-trimethyl-1H-3,9b-methanodibenzofuran-8-yl)-;

6-[Hydroxy-(5,5,8,8-tetramethyl-5,6,7,8-tetrahydro-naphthalen- 2-yl)-methyl]-naphthalene-2-carboxylic acid;

6-[Acetoxy-(5,5,8,8-tetramethyl-5,6,7,8-tetrahydro-naphthalen- 2-yl)-methyl]-naphthalene-2-carboxylic acid;

6-(1,1,3,3-Tetramethyl-indane-5-carbonyl)-naphthalene-2-carboxylic acid;

6-[Hydroxy-(1,1,2,3,3-pentamethyl-indan-5-yl)-methyl]-naphthalene-2-carboxylic acid;

6-(6,7-Dimethyl-naphthalene-2-carbonyl)-naphthalene-2-carboxylic acid;

6-(6-Methoxy-naphthalene-2-carbonyl)-naphthalene-2-carboxylic acid;

6-(6-Methoxy-5,8-dimethyl-naphthalene-2-carbonyl)-naphthalene-2-carboxylic acid;

6-[Hydroxy-(6-methoxy-5,8-dimethyl-naphthalen-2-yl)-methyl]-naphthalene-2-carboxylic acid;

6-(6-Methoxy-5,8-dimethyl-naphthalen-2-ylmethyl)-naphthalene-2-carboxylic acid;

6-(4,4-Dimethyl-chroman-6-carbonyl)-naphthalene-2-carboxylic acid;

6-[(4,4-Dimethyl-chroman-6-yl)-hydroxy-methyl]-naphthalene-2-carboxylic acid;

6-(4,4-Dimethyl-chroman-6-ylmethyl)-naphthalene-2-carboxylic acid;

2-Naphthalenecarboxylic acid, 6-[(2,3,4,4a-tetrahydro-4a,10,10-trimethyl-1H-3,9b-methanodibenzofuran-8-yl)carbonyl]-;

6-(2,2-Dimethyl-chroman-6-carbonyl)-naphthalene-2-carboxylic acid;

6-(4-tert-Butyl-benzoyl)-naphthalene-2-carboxylic acid;

6-[(2,4-Di-tert-butyl-phenyl)-hydroxy-methyl]-naphthalene-2-carboxylic acid;

6-(2,4-Diisopropyl-benzoyl)-naphthalene-2-carboxylic acid;

6-(2,4-Diisopropyl-benzyl)-naphthalene-4-carboxylic acid;

6-(4-Cyclohexyl-benzoyl)-naphthalene-2-carboxylic acid;

6-(4-Phenoxy-benzoyl)-naphthalene-2-carboxylic acid;

6-(4-Methoxy-benzoyl)-naphthalene-2-carboxylic acid;

6-(6-Methoxy-biphenyl-3-carbonyl)-naphthalene-2-carboxylic acid;

6-(3-Adamantan-1-yl-4-methoxy-benzoyl)-naphthalene-2-carboxylic acid;

6-(4-Methoxy-2,3,6-trimethyl-benzoyl)-naphthalene-2-carboxylic acid;

2-(1,1,3,3-Tetramethyl-indane-5-carbonyl)-benzoic acid;

2-(1,1,2,3,3-Pentamethyl-indane-5-carbonyl)-benzoic acid;

2-(3,6-Dimethoxy-tricyclo[6.2.1.0>2,7_]undeca-(7),3,5-triene-4-carbonyl)-benzoic acid;

2-(1,1,2,3,3-Pentamethyl-indane-5-carbonyl)-cyclohex-1-enecarboxylic acid;

2-(5,5,8,8-Tetramethyl-5,6,7,8-tetrahydro-naphthalene-2-carbonyl)-cyclohexanecarboxylic acid;

2-(1,1,2,3,3-Pentamethyl-indane-5-carbonyl)-cyclohexanecarboxylic acid;

4-(Tricyclo[6.2.1.0>2,7_]undeca-2(7),3,5-triene-4-carbonyl)-benzoic acid;

4-(1,1,2,3,3-Pentamethyl-indane-5-carbonyl)-benzoic acid;

4-[Hydroxy-(5,5,8,8-tetramethyl-5,6,7,8-tetrahydro-naphthalen-2-yl)-methyl]-benzoic acid;

4-(2,4-Diisopropyl-benzoyl)-benzoic acid;

4-[(2,4-Diisopropyl-phenyl)-hydroxy-methyl]-benzoic acid;

4-(3,5-Di-tert-butyl-4-hydroxy-benzoyl)-benzoic acid;

4-[Hydroxy-(6-methoxy-5,8-dimethyl-naphthalen-2-yl)-methyl]-benzoic acid;

4-[(4,4-dimethyl-thiochroman-6-yl)-hydroxymethyl]-benzoic acid;

4-(3-Oxo-3-phenyl-propenyl)-benzoic acid;

4-[3-(3,4-Diethyl-phenyl)-3-oxo-propenyl]-benzoic acid;

4-[3-(3,4-Diisopropyl-phenyl)-3-oxo-propenyl]-benzoic acid;

4-[3-(4-tert-Butyl-phenyl)-3-oxo-propenyl]-benzoic acid;

4-[3-(3-tert-Butyl-phenyl)-3-oxo-propenyl]-benzoic acid;

4-[3-(3,5-Di-tert-butyl-phenyl)-3-oxo-propenyl]-benzoic acid;

4-[3-(2,5-Di-tert-butyl-phenyl)-3-oxo-propenyl]-benzoic acid;

4-[3-Oxo-3-(5,5,8,8-tetramethyl-5,6,7,8-tetrahydro-naphthalen- 2-yl)-propenyl]-benzoic acid;

4-[3-Oxo-3-(3,5,5,8,8-pentamethyl-5,6,7,8-tetrahydro-naphthalen-2-yl)-propenyl]-benzoic acid;

2-Hydroxy-4-[3-oxo-3-(5,5,8,8-tetramethyl-5,6,7,8-tetrahydro-naphthalen-2-yl)-propenyl]-benzoic acid;

4-[3-(4,4-Dimethyl-chroman-6-yl)-3-oxo-propenyl]-benzoic acid;

4-[3-(4,4-Dimethyl-chroman-7-yl)-3-oxo-propenyl]-benzoic acid;

4-[3-(4,4-Dimethyl-thiochroman-6-yl)-3-oxo-propenyl]-benzoic acid;

4-[3-(3,4-Dimethoxy-phenyl)-3-oxo-propenyl]-benzoic acid;

4-[1-Hydroxy-3-(2-hydroxy-phenyl)-3-oxo-propenyl]-benzoic acid;

4-[3-(5-tert-Butyl-2-hydroxy-phenyl)-1-hydroxy-3-oxo-propenyl]-benzoic acid; and 4-[3-(4-tert-butyl-2-hydroxy-phenyl)-1-hydroxy-3-oxo-propenyl]-benzoic acid.

Other retinoids which can be utilized to lower plasma levels of Lp(a) include polyolefinic carboxylic acids, aldehydes, and alcohols having the general formula

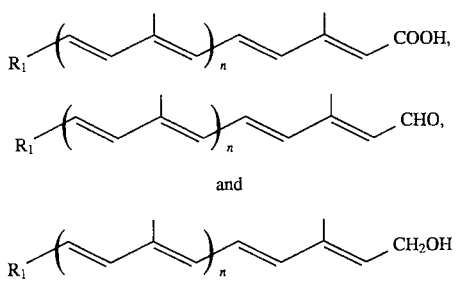

where $R_1$ includes the cycloalkyl and aryl groups such as those described above, and n is 0 or 1.

Typical $R_1$ groups additionally include the following: alkyl such as ethyl and hexyl; cycloalkyl such as cyclohexyl, alkylcyclohexyl, dialkylcyclohexyl, cyclohexenyl, cyclopentyl, dialkylcyclopentyl, cyclopentenyl, mono-and dialkylcyclopentyl; and aryl such as phenyl, hydroxyphenyl, methoxyphenyl, halophenyl, thienyl, furanyl, pyridyl, and polycyclic systems, such as

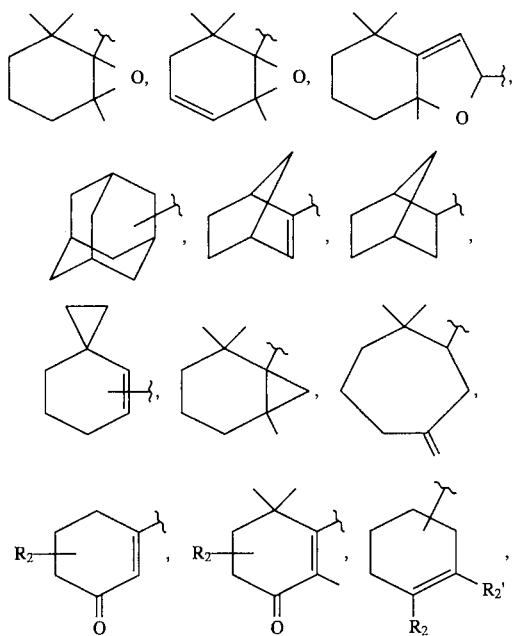

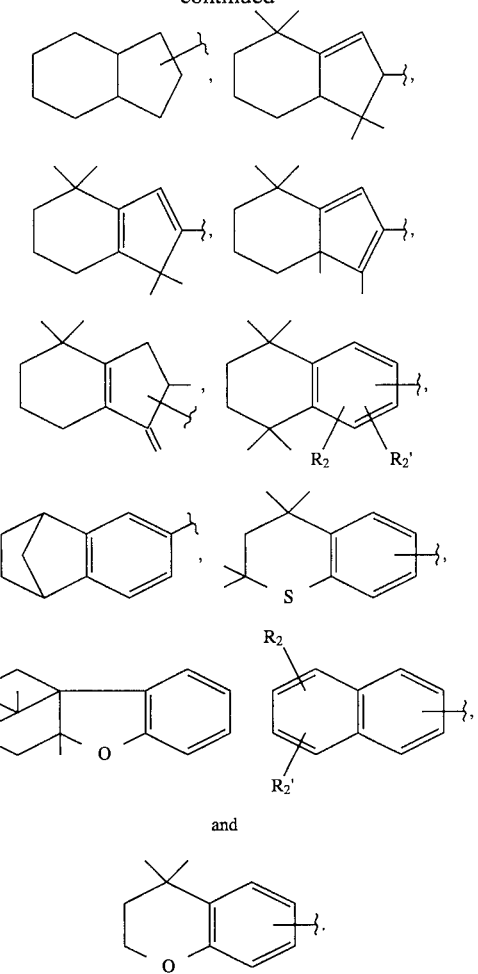

The retinoids to be utilized in this invention also include the various stereochemical isomers, for example, the all transisomers (E,E,E,E), the 9-cis isomers (E,E,Z,E), and the 13-cis isomers (Z,E,E,E).

Typical retinoids of the above class which can be utilized to lower Lp(a) include the following:

3,7-Dimethyl-undeca-2,4,6,8-tetraenal;

9-Cyclohexyl-3,7-dimethyl-nona-2,4,6,8-tetraenal;

3,7-Dimethyl-9-(2,2,6-trimethyl-cyclohexyl)-nona-2,4,6,8-tetraenal;

9-Cyclohex-1-enyl-3,7-dimethyl-nona-2,4,6,8-tetraenal;

3,7-Dimethyl-9-(2-methyl-cyclohex-1-enyl)-nona-2,4,6,8-tetraenal;

9-(6,6-Dimethyl-cyclohex-1-enyl)-3,7-dimethyl-nona-2,4,6,8-tetraenal;

3,7-Dimethyl-9-(2,6,6-trimethyl-cyclohex-1-enyl)-nona-2,4,6,8-tetraenal;

9-(2,6-Dimethyl-cyclohex-1-enyl)-3,7-dimethyl-nona-2,4,6,8-tetraenal;

3-Methyl-9-(2,5,5-trimethyl-cyclopent-1-enyl)-nona-2,4,6,8-tetraenal;

10-Isopropyl-3-methyl-dodeca-2,4,6,8,10-pentaenal;

3-Methyl-dodeca-2,4,6,8,10-pentaenal;

3,7-Dimethyl-9-(2,6,6-trimethyl-cyclohexa-1,3-dienyl)-nona-2,4,6,8-tetraenal;

3,7-Dimethyl-9-phenyl-nona-2,4,6,8-tetraenal;

9-(3-Hydroxy-2,6,6-trimethyl-cyclohex-1-enyl)-3,7-dimethyl-nona-2,4,6,8-tetraenal;

3,7-Dimethyl-9-(2,6,6-trimethyl-3-oxo-cyclohex-1-enyl)-nona-2,4,6,8-tetraenal;

3,7-Dimethyl-9-(2,2,6-trimethyl-7-oxa-bicyclo[4.1.0]hept-1-yl)-nona-2,4,6,8-tetraenal;

3,7-Dimethyl-9-(2,2,6-trimethyl-7-oxa-bicyclo[4.1.0]hept-4-en-1-yl)-nona-2,4,6,8-tetraenal;

9-(4-Methoxy-2,3,6-trimethyl-phenyl)-3,7-dimethyl-nona-2,4,6,8-tetraenal;

3-Methyl-9-(2,4,5-trimethyl-thiophen-3-yl)-nona-2,4,6,8-tetraenal;

3,7-dimethyl-9-(2,6,6-trimethylcyclohex-1-enzyl)-nona-2,4,6,7-tetraen-1-ol;

All trans-9-(4-Dimethylamino-phenyl)-3,7-dimethyl-nona-2,4,6,8-tetraenal;

3,7,11-Trimethyl-dodeca-2,4,6,8,10-pentaenal; 3,7-Dimethyl-9-(2,2,6-trimethyl-cyclohexylidene)-nona-2,4,6,8-tetraenal;

3-Methyl-7-(4,4,7a-trimethyl-2,4,5,6,7,7a-hexahydro-benzofuran-3-yl)-octa-2,4,6-trienal;

9-(2,2-Dimethyl-6-methylene-cyclohexyl)-3,7-dimethyl-nona-2,4,6,8-tetraenal;

9-Adamantan-2-ylidene-3,7-dimethyl-nona-2,4,6,8-tetraenal;

5,9-Dimethyl-11-(2,6,6-trimethyl-cyclohex-1-enyl)-undeca-2,4,6,8,10-pentaenal;

3,7-Dimethyl-9-(2,6,6-trimethyl-cyclohex-1-enyl)-nona-2,4,8-trienal;

3,7-Dimethyl-9-(2,6,6-trimethyl-cyclohex-1-enyl)-nona-2,8-dienal;

3,7-Dimethyl-9-(2,6,6-trimethyl-cyclohex-1-enyl)-nona-2,4,6-trienal;

3,7-Dimethyl-9-(2,6,6-trimethyl-cyclohex-1-enyl)-nona-2,6, 8-trien-1-ol;

2,7-Dimethyl-9-(2,6,6-trimethyl-cyclohex-1-enyl)-nona-2,4 ,6,8-tetraenal;

13-(2,6,6-Trimethyl-cyclohex-1-enyl)-trideca-2,4,6,8,10,12-hexaenal;

17-(2,6,6-Trimethyl-cyclohex-1-enyl)-heptadeca-2,4,6,8,10,12,14,16-octaenal;

7-Ethyl-3-methyl-9-(2,6,6-trimethyl-cyclohex-1-enyl)-nona-2,4,6,8-tetraenal;

2,3,7-Trimethyl-9-(2,6,6-trimethyl-cyclohex-1-enyl)-nona-2,4,6,8-tetraenal;

7-Methyl-9-(2,6,6-trimethyl-cyclohex-1-enyl)-nona-2,4,6,8-tetraenal;

2,7-Dimethyl-9-(2,6,6-trimethyl-cyclohex-1-enyl)-nona-2,4,6,8-tetraen-1-ol;

(E,E,E)-3,7-dimethyl-undeca-2,6,8-trien-4-yn-1-ol;

(Z,E,E)-3,7-dimethyl-undeca-2,6,8-trien-4-yn-1-ol;

(E,E,E)-2,2,7-trimethyl-3-methylene-undeca-4,6,8-trienoic acid;

(Z,E,E)-2,3,7-trimethyl-undeca-2,4,6,8-tetraenoic acid;

7-Methyl-9-(2,6,6-trimethyl-cyclohex-1-enyl)-nona-2,4,6,8-tetraenal;

{5-[1-Methyl-3-(2,6,6-trimethyl-cyclohex-1-enyl)-allylidene]-cyclohept-3-enylidene}-acetaldehyde;

{4-[1-Methyl-3-(2,6,6-trimethyl-cyclohex-1-enyl)-allylidene]-cyclohept-2-enylidene}-acetaldehyde;

3-Bromo-7-methyl-9-(2,6,6-trimethyl-cyclohex-1-enyl)-nona-2,4,6,8-tetraenal;

6-Fluoro-7-methyl-9-(2,6,6-trimethyl-cyclohex-1-enyl)-nona-2,4,6,8-tetraenal;

7-Methyl-9-(2,6,6-trimethyl-cyclohex-1-enyl)-nona-4,6,8-trien-2-ynal;

6,7-Dimethyl-9-(2,6,6-trimethyl-cyclohex-1-enyl)-nona-2,4,6,8-tetraenal;

3-Methyl-9-(2,6,6-trimethyl-cyclohex-1-enyl)-nona-2,4,6,8-tetraenal;

9-(2,6,6-Trimethyl-cyclohex-1-enyl)-nona-2,4,6,8-tetraenal;

7-Methyl-9-(2,6,6-trimethyl-cyclohex-1-enyl)-nona-2,4,6,8-tetraenal;

{5-[1-Methyl-3-(2,6,6-trimethyl-cyclohex-1-enyl)-allylidene]-cyclohept-3-enylidene}-acetaldehyde;

{4-[1-Methyl-3-(2,6,6-trimethyl-cyclohex-1-enyl)-allylidene]-cyclohept-2-enylidene}-acetaldehyde;

4,8-Dimethyl-10-(2,6,6-trimethyl-cyclohex-1-enyl)-deca-3,5,7,9-tetraen-2-one;

2-Bromo-3,7-dimethyl-9-(2,6,6-trimethyl-cyclohex-1-enyl)-nona-2,4,6,8-tetraenal;

2-Fluoro-3,7-dimethyl-9-(2,6,6-trimethyl-cyclohex-1-enyl)-nona-2,4,6,8-tetraenal;

3,7-Dimethyl-9-(2,6,6-trimethyl-cyclohex-1-enyl)-nona-2,4,6,8-tetraenoic acid;

3-Methyl-6-(1,1,4,4-tetramethyl-1,4,5,6,7,7a-hexahydro-inden-2-ylidene)-hexa-2,4-dienoic acid;

3-Methyl-e-(1,1,4,4-tetramethyl-1,4,5,6,7,7a-hexahydro-inden-2-ylidene)-hexa-2,4-dienoic acid;

(E,Z,E,E)-3-tert.-butyl-7-methyl-undec-2,4,6,8-tetraen-1-ol;

3-Methyl-6-(1,1,4,4-tetramethyl-4,5,6,7-tetrahydro-1H-inden-2-yl)-hexa-3,5-dienoic acid;

3-Methyl-6-(1,1,4,4-tetramethyl-4,5,6,7-tetrahydro-1H-inden-2-yl)-hexa-3,5-dienoic acid;

3-Methyl-6-(3,3a,7,7-tetramethyl-4,5,6,7-tetrahydro-3aH-inden-2-yl)-hexa-3,5-dienoic acid;

3-Methyl-6-(3,3a,7,7-tetramethyl-4,5,6,7-tetrahydro-3aH-inden-2-yl)-hexa-3,5-dienoic acid;

3-Methyl-6-(2,4,4-trimethyl-1-methylene-2,3,4,5,6,7-hexahydro-1H-inden-2-yl)-hexa-2,4-dienoic acid;

2,3,7-trimethyl-9-(2,6,6-trimethyl-cyclohexa-1,3-dienyl)-nona-2,4,6,8-tetraenoic acid;

9-(4-dimethylaminophenyl)-2,3,7-trimethyl-nona-2,4,6,8-tetraenoic acid; and

3-Methyl-6-(2,4,4-trimethyl-1-methylene-2,3,4,5,6,7-hexahydro-1H-inden-2-yl)-hexa-2,4-dienoic acid.

Additional retinoids which can be utilized are aryldienoic acids of the general formula

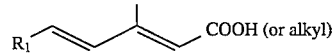

where $R_1$ is aryl, especially phenyl substituted with further aryl, cycloalkyl, and fused cycloalkylaryl groups.

Preferred retinoids have the formula

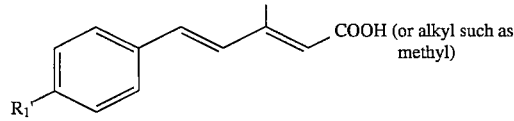

where $R_1$, is aryl, cycloalkyl, or polyclyclo of the following general formulas:

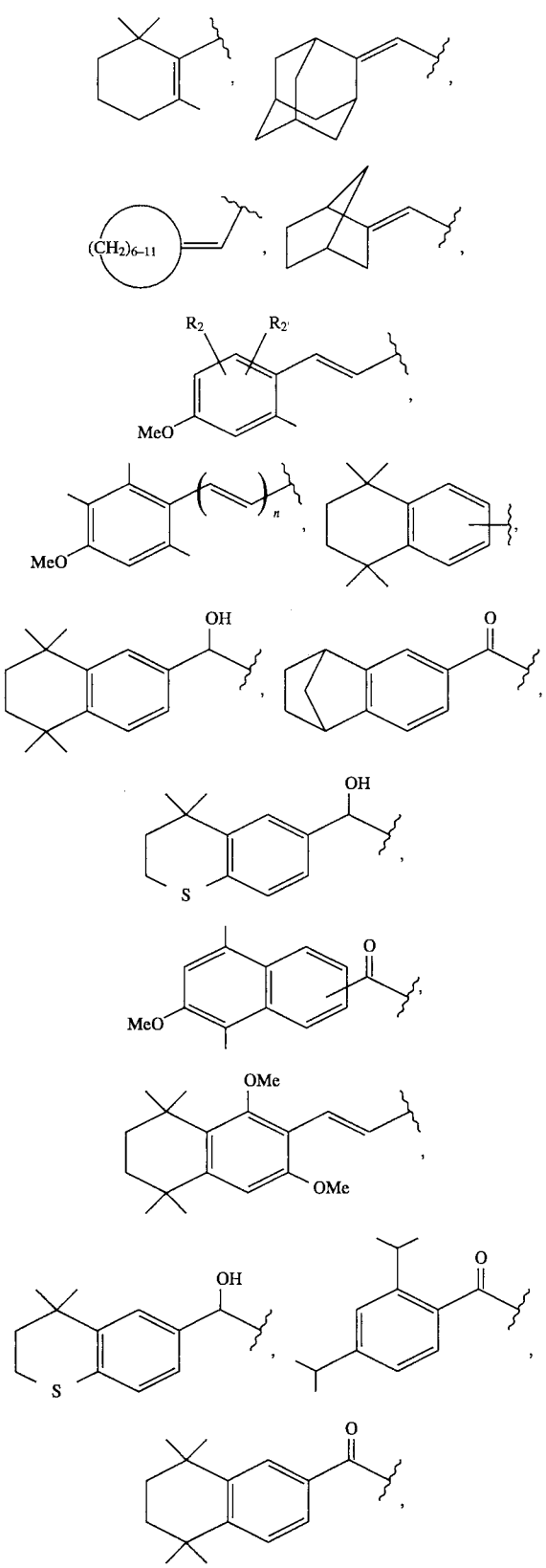

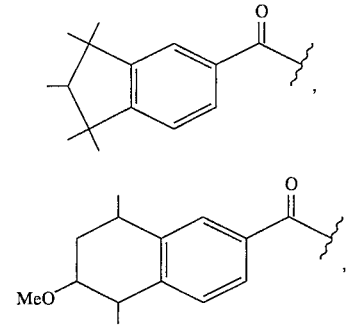

Specific retinoids included within the above general formulas include the following:

5-(4-Cycloundecylidenemethyl-phenyl)-3-methyl-penta-2,4-dienoic acid;

5-(4-Bicyclo[2.2.1]hept-2-ylidenemethyl-phenyl)-3-methyl-penta-2,4-dienoic acid;

5-{4-[2-(4-Methoxy-2,3,6-trimethyl-phenyl)-vinyl]-phenyl }- 3-methyl-penta-2,4-dienoic acid;

2,4-Pentadienoic acid, 3-methyl-5-(2,3,4,4a-tetrahydro-4a, 10,10-trimethyl-1H-3,9b-methanodibenzofuran-8-yl)-;

3-{4-[2-(4-Methoxy-2,3,6-trimethyl-phenyl)-vinyl]-phenyl }-acrylic acid;

3-{4-[4-(4-Methoxy-2,3,6-trimethyl-phenyl)- 2-methyl-buta-1,3-dienyl]-phenyl }-acrylic acid;

3-{4-[2-(1,3-Dimethoxy-5,5,8,8-tetramethyl-5,6,7,8-tetrahydro-naphthalen-2-yl)-vinyl]-phenyl}-acrylic acid;

3-{4-[Hydroxy-(5,5,8,8-tetramethyl-5,6,7,8-tetrahydro-naphthalen- 2-yl)-methyl]-phenyl}-acrylic acid;

3-{4-[(4,4-Dimethyl-thiochroman-6-yl)-hydroxy-methyl] -phenyl }-2-methyl-acrylic acid;

3-[4-(1,2,3,4-Tetrahydro-1,4-methano-naphthalene-6-carbonyl)-phenyl]-acrylic acid;

3-[4-(2,4-Diisopropyl-benzoyl)-phenyl]-2-methyl-acrylic acid;

3-[4-(5,5,8,8-Tetramethyl-5,6,7,8-tetrahydro-naphthalene-2-carbonyl)-phenyl]-acrylic acid;

2-Methyl-3-[4-(5,5,8,8-tetramethyl-5,6,7,8-tetrahydro-naphthalene-2-carbonyl)-phenyl]-acrylic acid;

2-Methyl-3-[4-(1,1,2,3,3-pentamethyl-indane-5-carbonyl-carbonyl)-phenyl]-acrylic acid;

3-[4-(4-Methoxy-2,5-dimethyl-benzoyl)-phenyl]-2-methyl-acrylic acid;

{2-[3-Methyl-5-(2,6,6-trimethyl-cyclohex-1-enyl)-penta-2,4-dienylidene]-cycloheptylidene}-acetaldehyde;

2-Methyl-3-[3-methyl-5-(2,6,6-trimethyl-cyclohex-1-enyl)-penta-2,4-dienylidene]-cyclopent-1-enecarbaldehyde;

3-Methyl-4-{3-[2-(2,6,6-trimethyl-cyclohex- 1-enyl)-vinyl]-cyclohex-2-enylidene}-but-2-enal;

{2-[3-Methyl-5-(2,6,6-trimethyl-cyclohex-1-enyl)-penta-2,4-dienylidene]-cyclohexylidene}-acetaldehyde;

{3-[2-Methyl-4-(2,6,6-trimethyl-cyclohex-1-enyl)-buta-1,3-dienyl]-cyclohex-2-enylidene}-acetaldehyde;

{4-[1-Methyl-3-(2,6,6-trimethyl-cyclohex-1-enyl)-allylidene]-cyclohept- 2-enylidene}-acetaldehyde; and {4-[1-Methyl-3-(2,6,6-trimethyl-cyclohex-1-enyl)-al-lylidene]-cyclopent- 2-enylidene}-acetaldehyde.

Still other compounds which are included within the general class of retinoids are retinoidal oxiranes, such as

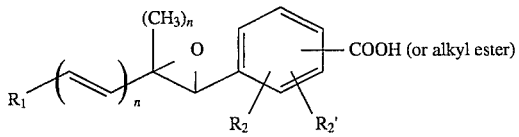

with preferred oximes having the formula:

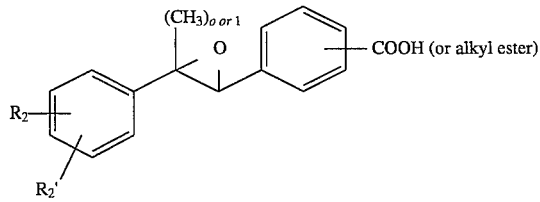

Typical retinoidal oxiranes include

4-[3-(4-tert-Butyl-phenyl)-oxiranyl]-benzoic acid;

4-[3-(3-tert-Butyl-phenyl)-oxiranyl]-benzoic acid;

4-[3-(3,4-Diethyl-phenyl)-3-methyl-oxiranyl]-benzoic acid; and

4-[3-Methyl-3-(5,5,8,8-tetra-methyl-5,6,7,8-tetrahydro-naphthalen-2-yl)-oxiranyl]-benzoic acid.

Related compounds are diketones, diols, and acetonides of the formula

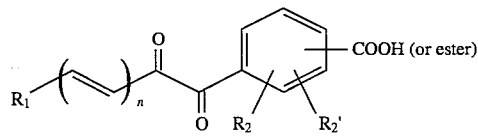

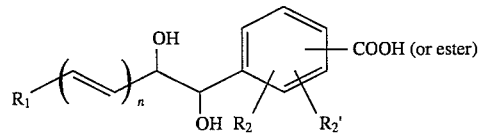

and

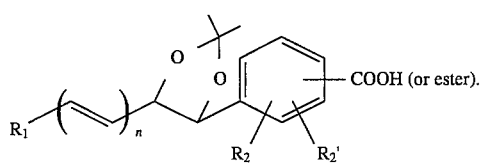

Certain retinoids have a carboxyamide linkage rather than an alkylene or oxidized alkylene. For example, carboxamide retinoids which can be utilized include those of the formula

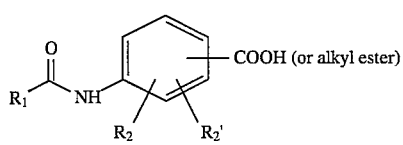

where $R_1$ is an organic radical and includes groups such as

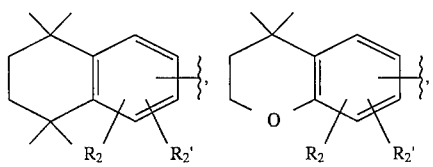

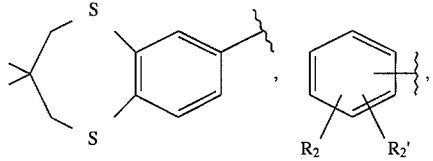

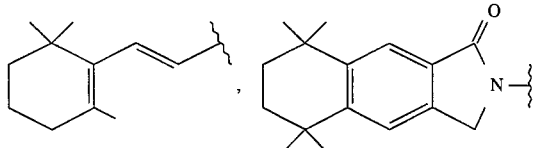

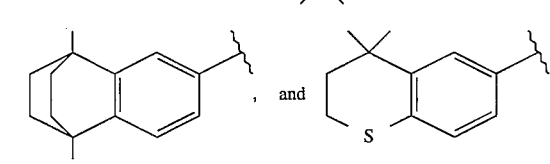

Typical carboxamide retinoids which can be utilized include 4-benzoylamino-benzoic acid;

3-tert-Butyl-benzoylamino)-benzoic acid;

4-tert-Butyl-benzoylamino)-benzoic acid;

4-(3,5-Di-tert-butyl-benzoylamino)-benzoic acid;

4-(3,4-Diisopropyl-benzoylamino)-benzoic acid;

4-[(5,5,8,8-Tetramethyl-5,6,7,8-tetrahydro-naphthalene-2-carbonyl)-amino]-benzoic acid;

4-[Methyl-5,5,8,8-tetramethyl-5,6,7,8-tetra-hydro-naphthalene-2-carbonyl)-amino]-benzoic acid;

4-[(4,4-Dimethyl-chroman-7-carbonyl)-amino]benzoic acid;

4-[(5-Chloro-4,4-dimethyl-chroman-7-carbonyl)-amino]-benzoic acid;

4-[(2,3-Dihydro-benzo[1,4]dioxine-6-carbonyl)-amino]-benzoic acid;

4-[(3,3-Dimethyl-3,4-dihydro-2H-benzo[b]-[1,4]diox-epine-7-carbonyl)-amino]-benzoic acid;

4-[(5-Methyl-2,3,4,5-tetrahydro-benzo[b]thiepine-8-carbonyl)-amino]-benzoic acid;

4-[(4,4-Dimethyl-thiochroman-7-carbonyl)-amino]8-benzoic acid

4-[(Thiochroman-6-carbonyl)-amino]-benzoic acid;

4-[(2,3-Dihydro-benzo[1,4]dithiine-6-carbonyl)-amino]-benzoic acid;

4-[(4,4-Dimethyl-1,1-dioxo-1l>6_-thiochroman-7-carbonyl)-amino]-benzoic acid;

4-[(3-Methyl-1,1-dioxo-1l>6_-thiochroman-6-carbonyl)-amino]-benzoic acid;

4-[(1,4,4-Trimethyl-1,2,3,4-tetrahydro-quinoline-7-carbonyl)-amino]-benzoic acid;

4-[(1-Decyl-4,4-dimethyl-1,2,3,4-tetrahydro-quinoline-7-carbonyl)-amino]-benzoic acid;

4-(3-tert-Butyl-4-methoxy-benzoylamino)-benzoic acid;

4-(3-Adamantan-1-yl-4-hydroxy-benzoylamino)-benzoic acid;

4-(3-Adamantan-1-yl-4-methoxy-benzoylamino)-benzoic acid;

4-(3-Adamantan-1-yl-4-methoxy-benzoylamino)-2-hydroxy-benzoic acid;

4-(3-Adamantan-1-yl-4-hexyloxy-benzoylamino)-benzoic acid;

4-(3-Adamantan-1-yl-4-decyloxy-benzoylamino)-benzoic acid;

4-[3-(1,1-Dimethyl-decyl)-4-methoxy-benzoylamino]-benzoic acid;

N-Phenyl-terephthalamic acid;

N-m-Tolyl-terephthalamic acid;

N-(3-Ethyl-phenyl)-terephthalamic acid;

N-(3-Isopropyl-phenyl)-terephthalamic acid;

N-(4-Isopropyl-phenyl)-terephthalamic acid;

N-(3-tert-Butyl-phenyl)-terephthalamic acid;

N-(4-tert-Butyl-phenyl)-terephthalamic acid;

4N-(3-Cyclohexyl-phenyl)-terephthalamic acid;

4N-Biphenyl-3-yl-terephthalamic acid;

N-(3-Bromo-phenyl)-terephthalamic acid;

N-(3-Dimethylamino-phenyl)-terephthalamic acid;

N-(3-Trifluoromethyl-phenyl)-terephthalamic acid;

N-(3,4-Diethyl-phenyl)-terephthalamic acid;

N-(2-Isopropyl-phenyl)-terephthalamic acid;

N-(2,4-Diisopropyl-phenyl)-terephthalamic acid;

N-(2,5-Diisopropyl-phenyl)-terephthalamic acid;

N-(2,6-Diisopropyl-phenyl)-terephthalamic acid;

N-(3,4-Diisopropyl-phenyl)-terephthalamic acid;

N-(3,5-Diisopropyl-phenyl)-terephthalamic acid;

N-(2,4-Di-tert-butyl-phenyl)-terephthalamic acid;

N-(3,5-Di-tert-butyl-phenyl)-terephthalamic acid;

N-(3,4-Dichloro-phenyl)-terephthalamic acid;

N-(5,6,7,8-Tetrahydro-naphthalen-1-yl)-terephthalamic acid;

N-(5,6,7,8-Tetrahydro-naphthalen-2-yl)-terephthalamic acid;

N-(5,5,8,8-Tetramethyl-5,6,7,8-tetrahydro-naphthalen-1-yl)-terephthalamic acid;

N-(5,5,8,8-Tetramethyl-5,6,7,8-tetrahydro-naphthalen-2-yl)-terephthalamic acid;

N-(3,5,5,8,8-Pentamethyl-5,6,7,8-tetrahydro-naphthalen-2-yl)-terephthalamic acid;

N-Methyl-N-(5,5,8,8-tetramethyl-5,6,7,8-tetrahydro-naphthalen-2-yl)-terephthalamic acid;

N-Isopropyl-N-(5,5,8,8-tetramethyl-5,6,7,8-tetrahydro-naphthalen-2-yl)-terephthalamic acid; and N-(3-Bromo-5,5,8,8-tetramethyl-5,6,7,8-tetrahydro-naphthalen-2-yl)-terephthalamic acid.

Retinoids similar to the carboxamides are carboxy esters such as

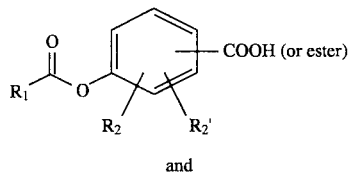

and

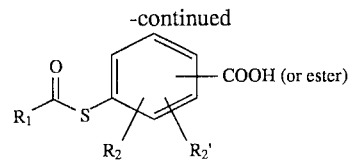

for example, where $R_1$ includes

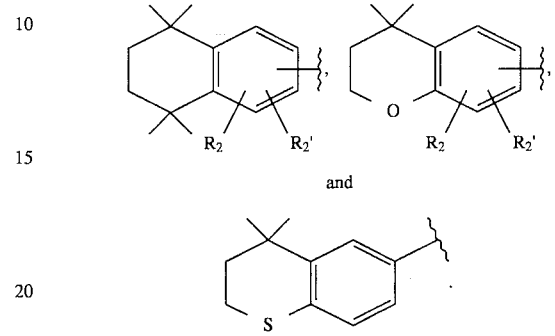

and

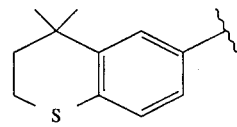

As noted before, any of these groups can be substituted in the ring system by $R_2$ and $R_2'$, as well as by other art-recognized substituent groups.

Typical (aroyloxy) benzoic acids and thio acids which can be utilized include

Benzoic acid, 3,5-bis (1,1-dimethylethyl)-4-hydroxy-, carboxyphenyl ester;

Benzoic acid, 4-ethyl-3-(tricyclo[3.3.1.1$^{3,7}$]dec-1-yl)-, 4-carboxyphenyl ester;

Benzoic acid, 4-ethenyl-3-(tricyclo[3.3.1.1$^{3,7}$]-dec-1-yl)-, 4-carboxyphenyl ester;

Benzoic acid, 4-methoxy-3-(tricyclo [3.3.1.1$^{3,7}$]-dec-1-yl)-, 4-carboxyphenyl ester;

Benzoic acid, 4-methoxy-3-(tricyclo [3.3.1.1$^{3,7}$]-dec-1-yl)-, 4-carboxy-3-methylphenyl ester;

Benzoic acid, 4-methoxy-3-(tricyclo [3.3.1.1$^{3,7}$]-dec-1-yl)-, 4-carboxy-2-(hydroxymethyl)phenyl ester;

4-(4-Adamantan-1-yl-3-methoxy-benzoyloxy) isophthalic acid;

Benzoic acid, 4-methoxy-3-(tricyclo[3.3.1.1$^{3,7}$]-dec-1-yl)-, 4-carboxy-3-hydroxyphenyl ester;

Benzoic acid, 2,4-dimethoxy-5-(tricyclo-[ 3.3.1.1$^{3,7}$]dec-1-yl)-, 4-carboxyphenyl ester;

Benzoic acid, 4-methoxy-3-(tricyclo[3.3.1.1$^{3,7}$]-dec-1-yl)-, 4-carboxy-2-methoxyphenyl ester;

Benzoic acid, 4-methoxy-3-(tricyclo[3.3.1.1$^{3,7}$]-dec-1-yl)-, 4-carboxy-3-methoxyphenyl ester;

Benzoic acid, 2-fluoro-4-methoxy-5-(tricyclo-]3.3.1.1$^{3,7}$] dec-1-yl)-, 4-carboxyphenyl ester;

Benzoic acid, 4-methoxy-3-(tricyclo[3.3.1.1$^{3,7}$]-dec-1-yl)-, 4-carboxy-3-fluorophenyl ester;

Benzoic acid, 4-(2-propenyloxy)-3-(tricyclo3.3.1.1$^{3,7}$] dec-1-yl)-, 4-carboxyphenyl ester;

Benzoic acid, 4-(acetyloxy)-3-(tricyclo-3.3.1.1$^{3,7}$]dec-1-yl)-, 4-carboxyphenyl ester;

Benzoic acid, 4-(2-methoxy-2-oxoethoxy)-3tricyclo-[ 3.3.1.1$^{3,7}$]dec-1-yl)-, 4-carboxyphenyl ester;

Benzoic acid, 4-[2-(phenylmethoxy)-2-oxoethoxy]-3-tricyclo[ 3.3.1.1$^{3,7}$]dec-1-yl)-, 4-carboxyphenyl ester;

Benzoic acid, 4-(methylsulfonyl)-3-(tricyclo-[3.3.1.1$^{3,7}$] dec-1-yl)-, 4-carboxyphenyl ester;

4,4-Dimethyl-chroman-6-carboxylic acid;
4-ethoxycarbonyl-phenyl ester;

2,2,4,4-Tetramethyl-chroman-6-carboxylic acid;
4-ethoxycarbonyl-phenyl ester;

2,2,4,4,7-Pentamethyl-chroman-6-carboxylic acid;
4-ethoxycarbonyl-phenyl ester;

4,4,7-Trimethyl-thiochroman-6-carboxylic acid;
4-ethoxycarbonyl-phenyl ester;

2,2,4,4-Tetramethyl-thiochroman-6-carboxylic acid;
4-ethoxycarbonyl-phenyl ester;

4-(5,5,8,8-Tetramethyl-5,6,7,8-tetrahydro-naphthalene-2-carbonylsulfanyl)-benzoic acid;

4-(3-Isopropyl-4-methoxy-benzoylsulfanyl)-benzoic acid;

4-(3-Isopropylsulfanyl-4-methyl-benzoylsulfanyl)-benzoic acid;

4-(3-Adamantan-1-yl-benzoylsulfanyl)-benzoic acid;

4-(5-Adamantan-1-yl-2-fluoro-4-methoxy-benzoylsulfanyl)-benzoic acid;

4-<5-Adamantan-1-yl-4-methoxy-2-methyl-benzoylsulfanyl)-benzoic acid;

4-(3-Adamantan-1-yl-4-allyloxy-benzoylsulfanyl)-benzoic acid;

4-(3-Adamantan-1-yl-4-methylsulfanyl-benzoylsulfanyl)-benzoic acid; and 4-(3 ,5-Bis-trifluoromethyl-benzoylsulfanyl)-benzoic acid.

Other benzoic acid derivatives which are retinoids and which can be utilized to lower Lp(a) according to this invention include (arylmethyl)amino benzoic acid, for example, compounds of the formulas

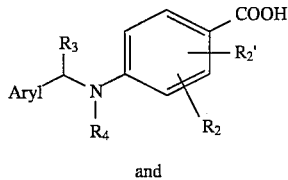

and

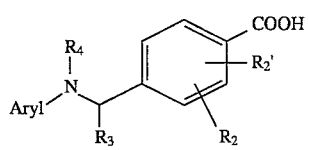

where aryl is an aromatic radical such as phenyl, naphthyl, thienyl, or the like, optionally substituted with from 1 to 5 substituents such as alkyl, alkenyl, alkynyl, halo, nitro, amino, mono-or dialkylamino, hydroxy, and the like, and $R_3$ and $R_4$ are hydrogen, alkyl, alkenyl, alkynyl, or the like.

Typical aryl methylamino benzoic acid retinoids from this class include 4-(4-tert-Butyl-benzylamino)-benzoic acid;

4-(3,5-Di-tert-butyl-4-hydroxy-benzylamino)-benzoic acid;

4-(4-tert-Butoxy-3-methoxy-benzylamino)-benzoic acid;

4-[4-(1-Methoxy-1-methyl-ethyl)-benzylamino]-benzoic acid;

4-[(5,5,8,8-Tetramethyl-5,6,7,8-tetrahydro-naphthalen-2-ylmethyl)-amino]-benzoic acid;

4-[(3-Fluoro-5,5,8,8-tetramethyl-5,6,7,8-tetrahydro-naphthalen- 2-ylmethyl)-amino]-benzoic acid;

4-[(3-Methoxy-5,5, 8,8-tetramethyl-5,6,7,8-tetrahydro-naphthalen-2-ylmethyl)-amino]-benzoic acid;

4-[(1,3-Dimethoxy-5,5,8,8-tetramethyl-5,6,7,8tetrahydro-naphthalen-2-ylmethyl)-amino]-benzoic acid;

4-[(1-Butoxy-3,5,5,8,8-pentamethyl-5,6,7,8-tetrahydro-naphthalen-2-ylmethyl)-amino]-benzoic acid;

4-[(5,5,8,8-Tetramethyl-5,8-dihydro-naphthalen-2-ylmethyl)-amino]-benzoic acid;

4-[(5,5,8,8-Tetramethyl-7-oxo-5,6,7,8-tetrahydro-naphthalen-2-ylmethyl)-amino]-benzoic acid;

4-[(7-Hydroxy-5,5,8,8-tetramethyl-5,6,7,8-tetrahydro-naphthalen-2-ylmethyl)-amino]-benzoic acid;

4-[1-(7-Hydroxy-5,5,8,8-tetramethyl-5,6,7,8-tetrahydro-naphthalen-2-yl)-ethylamino]-benzoic acid;

4-[Methyl-(5,5,8,8-tetramethyl-5,6,7,8-tetrahydro-naphthalen-2-ylmethyl)-amino]-benzoic acid;

4-[Acetyl-(5,5,8,8-tetramethyl-5,6,7,8-tetrahydro-naphthalen-2-ylmethyl)-amino]-benzoic acid;

4-[(5-tert-Butyl-2-methyl-phenylamino)-methyl]-benzoic acid;

4-[(3,5-Di-tert-butyl-phenylamino)-methyl]-benzoic acid;

4-[(4-tert-Butyl-2,6-dimethyl-phenylamino)-methyl]-benzoic acid;

4-[(1,1,2,3,3-Pentamethyl-indan-5-ylamino)-methyl]-benzoic acid;

4-[1-(5,5,8,8-Tetramethyl-5,6,7,8-tetrahydro-naphthalen-2-ylamino)-ethyl]-benzoic acid;

4-[(1,4-Dichloro-5,5,8,8-tetramethyl-5,6,7,8-tetrahydro-naphthalen-2-ylamino)-methyl]-benzoic acid;

4-[(1,4-Dimethoxy-5,5,8,8-tetramethyl-5,6,7,8-tetrahydro-naphthalen- 2-ylamino)-methyl]-benzoic acid; and 4-{[Acetyl-(1,4-dimethoxy-5,5,8,8-tetramethyl-5,6,7,8-tetrahydro-naphthalen-2-yl)-amino]-methyl}-benzoic acid.

Another preferred group of retinoids that are effective in lowering Lp(a) include (aryloxy)methyl benzoic acid of the formulas

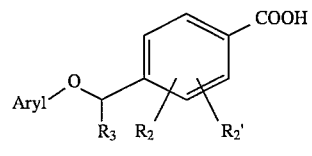

and

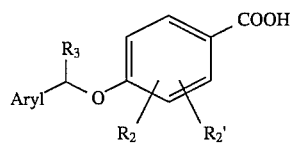

Typical members of this class include 4-(4-tert-Butyl-phenoxymethyl)-benzoic acid;

4-(3-tert-Butyl-phenoxymethyl)-benzoic acid;

4-[4-(1,1-Dimethyl-propyl)-phenoxymethyl]-benzoic acid;

4-(2-tert-Butyl-4-methyl-phenoxymethyl)-benzoic acid;

4-(4-tert-Butyl-2-methyl-phenoxymethyl)-benzoic acid;

4-(2,4-Di-tert-butyl-phenoxymethyl)-benzoic acid;

4-(2,6-Di-tert-butyl-phenoxymethyl)-benzoic acid;

4-(2,5-Di-tert-butyl-phenoxymethyl)-benzoic acid;

4-(3,5-Di-tert-butyl-phenoxymethyl)-benzoic acid;
4-(2-sec-Butyl-4-tert-butyl-phenoxymethyl)-benzoic acid;
4-(2,4-Di-tert-butyl-5-methyl-phenoxymethyl)-benzoic acid;
4-(2,4,6-Tri-tert-butyl-phenoxymethyl)-benzoic acid;
4-(3,5-Di-tert-butyl-2-hydroxy-phenoxymethyl)-benzoic acid;
4-(5,5,8,8-Tetramethyl-3-nitro-5,6,7,8-tetrahydro-naphthalen-2-yloxymethyl)-benzoic acid;
4-(1,4-Dihydroxy-5,5,8,8-tetramethyl-5,6,7,8-tetrahydro-naphthalen-2-yloxymethyl)-benzoic acid;
4-(1,4-Diacetoxy-5,5,8,8-tetramethyl-5,6,7,8-tetrahydro-naphthalen-2-yloxymethyl)-benzoic acid;
4-(2,2,5,7,8-Pentamethyl-chroman-6-yloxymethyl)-benzoic acid;
4-[2-(2-Hydroxy-ethyl)-2,5,7,8-tetramethylchroman-6-yloxymethyl]-benzoic acid; and
4-[2-(2-Acetoxy-ethyl)-2,5,7,8-tetramethylchroman-6-yloxymethyl]-benzoic acid.

Similar compounds which have sulfur in the linkage instead of oxygen include the following
4-(4-tert-Butyl-phenylsulfanylmethyl)-benzoic acid;
4-(4-tert-Butyl-2-methyl-phenylsulfanylmethyl)-benzoic acid;
4-(4-tert-Butyl-2-methyl-phenylsulfanylmethyl)-benzoic acid;
4-(4-tert-Butyl-2-methyl-phenylsulfanylmethyl)-benzoic acid;
4-(4-tert-Butyl-2-methyl-phenylsulfanylmethyl)-benzoic acid; and
4-(4-tert-Butyl-2-methyl-phenylsulfanylmethyl)-benzoic acid.

Like the carboxamides and esters, some retinoids have more than one nitrogen in the linking chain, for example, there are arylazobenzoic acids such as

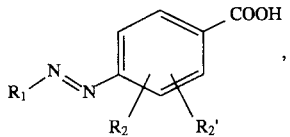

and hydrazone-bridge benzoic acids such as

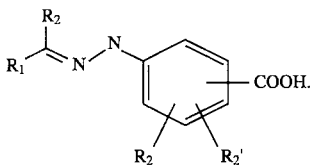

Typical members of this class include
4-(3,4-Diethyl-phenylazo)-benzoic acid;
4-(2-Isopropyl-phenylazo)-benzoic acid;
4-(3-Isopropyl-phenylazo)-benzoic acid;
4-(4-Isopropyl-phenylazo)-benzoic acid;
4-(2,4-Diisopropyl-phenylazo)-benzoic acid;
4-(2,6-Diisopropyl-phenylazo)-benzoic acid;
4-3,4-Diisopropyl-phenylazo)-benzoic acid;
4-3,5-Diisopropyl-phenylazo)-benzoic acid;
4-3-tert-Butyl-phenylazo)-benzoic acid;
4-3-Cyclohexyl-phenylazo)-benzoic acid;
4-(Biphenyl-3-ylazo)-benzoic acid;
(4,4-Dimethyl-thiochroman-6-ylazo)-benzoic acid;
4-[2-Hydroxy-2-(5,5,8,8-tetramethyl-5,6,7,8-tetrahydro-naphthalen-2-yl)-ethylamino]-benzoic acid;
4-[2-Hydroxy-2-(5,5,8,8-tetramethyl-5,6,7,8-tetrahydro-naphthalen- 2-yl)-ethylsulfanyl]-benzoic acid;
4-[2-Hydroxy-2-(5,5,8,8-tetramethyl-5,6,7,8-tetrahydro-naphthalen-2-yl)-ethoxy]-benzoic acid;
4-[N'-(5,5,8,8-Tetramethyl-5,6,7,8-tetrahydro-naphthalen-2-ylmethylene)-hydrazino]-benzoic acid; and
4-{N'-[Cyclopropyl-(1,1,2,3,3-pentamethyl-indan-5-yl)-methylene]-hydrazino}-benzoic acid.

A particular preferred class of retinoid compounds to be utilized to lower Lp(a) according to this invention include polyenoic acids and esters such as

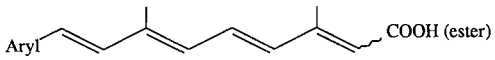

where aryl is an unsubstituted or substituted aromatic or cyclic radical such as phenyl, naphthyl, piperidyl, morpholinyl, or the like, and ester is preferably an alkyl group such as methyl, ethyl, isobutyl, or the like. Typical polyenoic retinoids include the following
3,7-Dimethyl-9-(2,6,6-trimethyl-cyclohex-1-enyl)-nona-2,4,6,8-tetraenoic acid methyl ester;
3,7-Dimethyl-9-(2,6,6-trimethyl-cyclohex-1-enyl)-nona-2,4,6,8-tetraenoic acid 2-{2-[2-(2-hydroxy-ethoxy)-ethoxy]-ethoxy}-ethyl ester;
3,7-Dimethyl-9-(2,6,6-trimethyl-cyclohex-1-enyl)-nona-2,4,6,8-tetraenoic acid 2-{2-[2-(2-hydroxyethoxy)-ethoxy]-ethoxy}-ethyl ester;
3,7-Dimethyl-9-(2,6,6-trimethyl-cyclohex-1-enyl)-nona-2,4,6,8-tetraenoic acid 2-(2-oxo-pyrrolidin-1-yl)-ethyl ester;
3,7-Dimethyl-9-(2,6,6-trimethyl-cyclohex-1-enyl)-nona-2,4,6,8-tetraenoic acid 2-(2-oxo-pyrrolidin-1-yl)-ethyl ester;
9-(4-Methoxy-2,3,6-trimethyl-phenyl)-3,7-dimethyl-nona- 2,4,6,8-tetraenoic acid 2-{2-[2-(2-hydroxy-ethoxy)-ethoxy]-ethoxy}-ethyl ester;
9-(4-Methoxy-2,3,6-trimethyl-phenyl)-3,7-dimethyl-nona- 2,4,6,8-tetraenoic acid 2-piperidin-1-yl-ethyl ester;
9-(4-Methoxy-2,3,6-trimethyl-phenyl)-3,7-dimethyl-nona- 2,4,6,8-tetraenoic acid 2-morpholin-4-yl-ethyl ester;
9-(4-Methoxy-2,3,6-trimethyl-phenyl)-3,7-dimethyl-nona- 2,4,6,8-tetraenoic acid 2-piperidin-1-yl-ethyl ester;
9-(4-Methoxy-2,3,6-trimethyl-phenyl)-3,7-dimethyl-nona- 2,4,6,8-tetraenoic acid 2-(2,5-dioxo-pyrrolidin-1-yl)-ethyl ester;
9-(4-Methoxy-2,3,6-trimethyl-phenyl)-3,7-dimethyl-nona- 2,4,6,8-tetraenoic acid 2-(2,6-dioxo-cyclohexyl)-ethyl ester;
9-(4-Methoxy-2,3,6-trimethyl-phenyl)-3,7-dimethyl-nona- 2,4,6,8-tetraenoic acid 2-methanesulfonyl-ethyl ester;
9-(4-Methoxy-2,3,6-trimethyl-phenyl)-3,7-dimethyl-nona- 2,4,6,8-tetraenoic acid methoxycarbonylmethyl ester;

9-(4-Methoxy-2,3,6-trimethyl-phenyl)-3,7-dimethyl-nona- 2,4,6,8-tetraenoic acid tert-butoxycarbonylmethyl ester;

9-(4-Methoxy-2,3,6-trimethyl-phenyl)-3,7-dimethyl-nona - 2,4,6,8-tetraenoic acid phenoxycarbonylmethyl ester;

9-(4-Methoxy-2,3,6-trimethyl-phenyl)-3,7-dimethyl-nona- 2,4,6,8-tetraenoic acid 2-acetoxy-phenoxycarbonyl methyl ester;

9-(4-Methoxy-2,3,6-trimethyl-phenyl)-3,7-dimethyl-nona - 2,4,6,8-tetraenoic acid styryloxycarbonylmethyl ester;

9-(4-Methoxy-2,3,6-trimethyl-phenyl)-3,7-dimethyl-nona- 2,4,6,8-tetraenoic acid 2-(4-methoxy-phenyl)-vinyloxycarbonylmethyl ester;

9-(4-Methoxy-2,3,6-trimethyl-phenyl)-3,7-dimethyl-nona- 2,4,6,8-tetraenoic acid 2-(benzoyl-carbonyl)-5-methoxy-phenoxymethoxycarbonyl-methyl ester;

9-(4-Methoxy-2,3,6-trimethyl-phenyl)-3,7-dimethyl-nona- 2,4,6,8-tetraenoic acid 1-phenoxycarbonyl-ethyl ester;

9-(4-Methoxy-2,3,6-trimethyl-phenyl)-3,7-dimethyl-nona - 2,4,6,8-tetraenoic acid 1-ethoxycarbonyloxy-ethyl ester;

3,7-Dimethyl-9-(2,6,6-trimethyl-cyclohex-1-enyl)-nona-2,4,6,8-tetraenoic acid 2-butoxy-4-dimethylamino-6-methyl-tetrahydro-pyran-3-yl ester;

3,7-Dimethyl-9-(2,6,6-trimethyl-cyclohex-1-enyl)-nona-2,4,6,8-tetraenoic acid 2-butoxy-4-dimethylamino-6-methyl-tetrahydro-pyran-3-yl ester;

3,7-Dimethyl-9-(2,6,6-trimethyl-cyclohex-1-enyl)-nona-2,4,6,8-tetraenoic acid 2-butoxy-4-dimethylamino-6-methyl-tetrahydro-pyran-3-yl ester;

3,7-Dimethyl-9-(2,6,6-trimethyl-cyclohex-1-enyl)-nona-2,4,6,8-tetraenoic acid 4-dimethylamino-6-methyl-2-(2-octyl-hexadecyloxy)-tetrahydro-pyran-3-yl ester;

9-(4-Methoxy-2,5,6-trimethyl-cyclohex-1-enyl)-3,7-dimethyl-nona-2,4,6,8-tetraenoic acid 2-butoxy-4-dimethylamino-6-methyl-tetrahydro-pyran-3-yl ester;

9-(4-Methoxy-2,5,6-trimethyl-cyclohex-1-enyl)-3,7-dimethyl-nona-2,4,6,8-tetraenoic acid 2-butoxy-4-dimethylamino-6-methyl-tetrahydro-pyran-3-yl ester; and 9-<4-Methoxy-2,5,6-trimethyl-cyclohex-1-enyl)-3,7-dimethyl-nona-2,4,6,8-tetraenoic acid 2-butoxy-4-dimethylamino-6-methyl-tetrahydro-pyran-3-yl ester.

In addition to retinoic acids and esters, the method of this invention can be practiced with retinoid amides, for example, any of the foregoing compounds in an amide form, e.g., the general formula

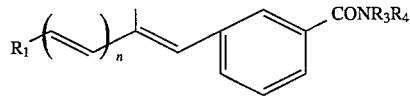

where $R_3$ and $R_4$ independently and hydrogen, $C_1$–$C_6$ alkyl, phenyl, or $R_2R_2'$ substituted or disubstituted phenyl, or taken together with the nitrogen to which they are attached, $R_3$ and $R_4$ complete a ring which can have 1 or 2 heteroatoms, such as oxygen, sulfur, or nitrogen. Typical retinoids of this type include

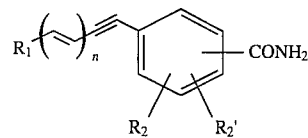

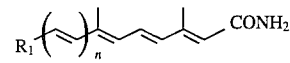

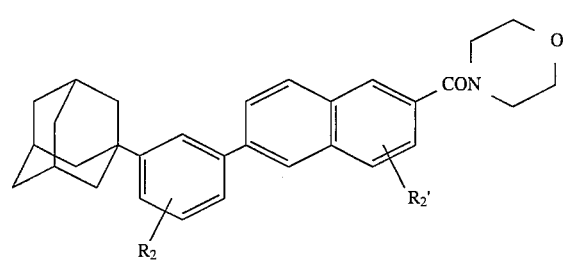

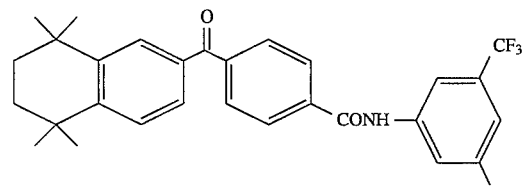

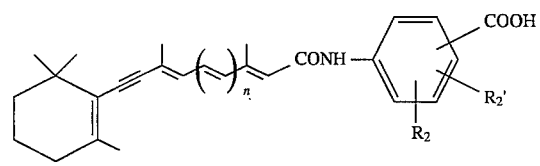

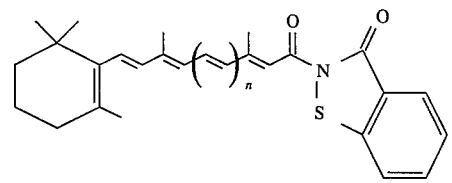

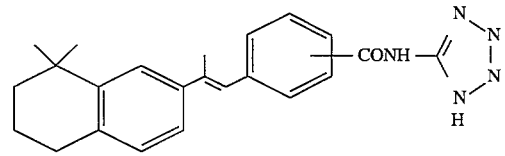

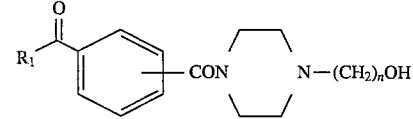

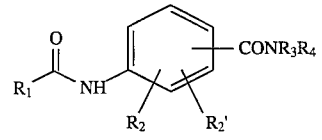

Examples of specific retinoids having the above structures include the following 4-[4-(2,6,6-Trimethyl-cyclohex-1-enyl)-but-3-en-1-ynyl]-benzamide;

3,7-Dimethyl-9-(2,6,6-trimethyl-cyclohex-1-enyl)-nona-2,4,6,8-tetraenoic acid amide;

[6-(3-Adamantan-1-yl-4-methoxy-phenyl)-naphthalen-2-yl]-morpholin-4-yl-methanone;

N-(3,5-Bis-trifluoromethyl-phenyl)-4-(5,5,8,8-tetramethyl- 5,6,7,8-tetrahydro-naphthalene-2-carbonyl)-benzamide;

N-(4-Hydroxy-phenyl)-4-[2-(5,5,8,8-tetramethyl-5,6,7,8-tetrahydro-naphthalen-2-yl)-vinyl]-benzamide;

N-<3,5-Bis-trifluoromethyl-phenyl)-4-(5,5,8,8-tetramethyl- 5,6,7,8-tetrahydro-naphthalene-2-carbonyl) benzamide;

[3,7-Dimethyl-9-(2,6,6-trimethyl-cyclohex-1-enyl)-nona-2,4,6,8-tetraenoylamino]-acetic acid;

[3,7-Dimethyl-9-(2,6,6-trimethyl-cyclohex-1-enyl)-nona-2,4,6,8-tetraenoylamino]-acetic acid methyl ester;

2-[3,7-Dimethyl-9-(2,6,6-trimethyl-cyclohex-1-enyl)-nona -2,4,6,8-tetraenoylamino]-4-methyl-pentanoic acid;

2-[3,7-Dimethyl-9-(2,6,6-trimethyl-cyclohex-1-enyl)-nona-2,4,6,8-tetraenoylamino]-3-phenyl-propionic acid;

2-[3,7-Dimethyl-9-(2,6,6-trimethyl-cyclohex-1-enyl)-nona -2,4,6,8-tetraenoylamino]-3-(4-hydroxy-phenyl)-propionic acid;

2-[3,7-Dimethyl-9-(2,6,6-trimethyl-cyclohex-1-enyl)-nona-2,4,6,8-tetraenoylamino]-pentanedioic acid;

[3,7-Dimethyl-9-(2,6,6-trimethyl-cyclohex-1-enyl)-nona-2,4,6,8-tetraenoylamino]-acetic acid;

2-[3,7-Dimethyl-9-(2,6,6-trimethyl-cyclohex-1-enyl)-nona- 2,4,6,8-tetraenoylamino]-propionic acid;

[3,7-Dimethyl-9-(2,6,6-trimethyl-cyclohex-1-enyl)-nona-2,4,6,8-tetraenoylamino]-4-methyl-pentanoic acid;

2-[3,7-Dimethyl-9-(2,6,6-trimethyl-cyclohex-1-enyl)-nona-2,4,6,8-tetraenoylamino]- 3-phenyl-propionic acid;

4-[3,7-Dimethyl-9-(3,3,6,6-tetramethyl-cyclohex-1-enyl)-nona- 2,4,6-trien-8-ynoylamino]-benzoic acid;

2-[3,7-Dimethyl-9-(2,6,6-trimethyl-cyclohex-1-enyl)-nona- 2,4,6,8-tetraenoyl]-benzo[d]isothiazol-3-one;

4-[2-(8,8-Dimethyl-5,6,7,8-tetrahydro-naphthalen-2-yl)-propenyl]-N-(1H-tetrazol- 5-yl)-benzamide;

[3,7-Dimethyl-9-(2,6,6-trimethyl-cyclohex-1-enyl)-nona-2,4,6,8-tetraenoylamino]-acetic acid;

4-Methyl-7-(5,5,8,8-tetramethyl-5,6,7,8-tetrahydro-naphthalen- 2-yl)-octa-2,4,6-trienoic acid ethylamide;

{4-[4-(2-Hydroxy-ethyl)-piperazine-1-carbonyl]-phenyl}-( 5,5,8,8-tetramethyl-5,6,7,8-tetrahydro-naphthalen-2-yl)-methanone;

6-(5,5,8,8-Tetramethyl-5,6,7,8-tetrahydro-naphthalene-2-carbonyl)-naphthalene-2-carboxylic acid; [2-(2-hydroxy-ethoxy)-ethyl]-amide;

6-(5,5,8,8-Tetramethyl-5,6,7,8-tetrahydro-naphthalene-2-carbonyl)-naphthalene-2-carboxylic acid (4-hydroxy-phenyl)-amide;

4-Methylsulfanyl-2-{[6-(5,5,8,8-tetramethyl-5,6,7,8-tetrahydro-naphthalene-2-carbonyl)-naphthalene-2-carbonyl]-amino}-butyric acid; p1 5-(4-Adamantan-2-ylidenemethyl-phenyl)-3-methyl-penta- 2,4-dienoic acid (2-ethyl-hexyl)-amide;

2-[5-(4-Adamantan-2-ylidenemethyl-phenyl)- 3-methyl-penta-2,4-dienoylamino]-4-methylsulfanyl-butyric acid ethyl ester;

4-[2-(1,3-Dimethoxy-5,5,8,8-tetramethyl-5,6,7,8-tetrahydro-naphthalen- 2-yl)-vinyl]-N-(2-hydroxy-ethyl)-benzamide;

N-Butyl-2-(5,5,8,8-tetramethyl-5,6,7,8-tetrahydro-naphthalene-2-carbonyl)-benzamide;

N-(2-Hydroxy-ethyl)-2-(5,5,8,8-tetramethyl-5,6,7,8-tetrahydro-naphthalene-2-carbonyl)-benzamide; and {2-[4-(2-Hydroxy-ethyl)-piperazine-1-carbonyl-carbonyl]-phenyl}-( 5,5,8,8-tetramethyl-5,6,7,8-tetrahydro-naphthalen-2-yl)-methanone.

An especially preferred group of retinoids for lowering Lp(a) are adamantyl substituted benzamides which can be prepared by reacting a compound such as 3-adamantan-1-yl-4-methoxy-benzoyl chloride with a 4-aminobenzamide according to the following sequence

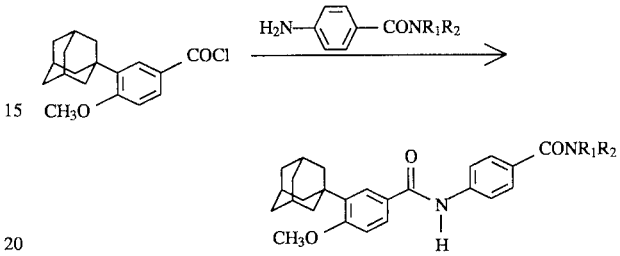

where $R_1$ and $R_2$ can be organic radicals such as $C_1$–$C_6$ alkyl, $C_2$–$C_6$ alkenyl, $C_2$–$C_6$ alkynyl, $C_3$–$C_6$ cycloalkyl, and the like, or together with the nitrogen form a cyclic ring such as pyrrolidine or the like.

Typical amino benzamide starting materials include

4-Amino-N-tert-butyl-benzamide;

4-Amino-N-phenyl-benzamide;

4-Amino-N-benzyl-benzamide;

4-Amino-N-(2-hydroxy-ethyl)-benzamide;

(4-Amino-phenyl)-pyrrolidin-1-yl-methanone;

(4-Amino-phenyl)-piperidin-1-yl-methanone; and (4-Amino-phenyl)-morpholin-4-yl-methanone.

Typical retinoids prepared as described above include

Benzamide, N-[4-[[(1,1-dimethylethyl) amino]-carbonyl]phenyl]- 4-methoxy-3-(tricyclo[3.3.1.1$^{3,7}$]dec-1-yl)-;

Benzamide, N-[4-[(phenylamino)carbonyl]phenyl]-4-methoxy-3-(tricyclo [3.3.1.1$^{3,7}$]dec-1-yl)-;

Benzamide, N-[4-[[(phenylmethyl)amino]carbonyl]-phenyl]-4-methoxy-3-(tricyclo[ 3.3.1.1$^{3,7}$]dec-1-yl)-;

Benzamide, N-[4-[[(2-hydroxyethyl)amino]carbonyl]-phenyl]-4-methoxy-3-(tricyclo [ 3.3.1.1$^{3,7}$]dec-1-yl)-;

3-Adamantan-1-yl-4-methoxy-N-[4-(pyrrolidine-1-carbonyl-carbonyl)-phenyl]-benzamide;

3-Adamantan-1-yl-4-methoxy-N-[4-(piperidine-1-carbonyl-carbonyl)-phenyl]-benzamide; and 3-Adamantan-1-yl-4-methoxy-N-[4-(morpholine-4-carbonyl-carbonyl)-phenyl]-benzamide.

The following specific retinoids are also useful in the method of this invention:

4-[3-(4-tert-Butyl-phenyl)-oxiranyl]-benzoic acid;

4-[3-(3-tert-Butyl-phenyl)-oxiranyl]-benzoic acid;

4-[3-(3,4-Diethyl-phenyl)-3-methyl-oxiranyl]benzoic acid;

4-[3-Methyl-3-(5,5,8,8-tetramethyl-5,6,7,8-tetrahydro-naphthalen-2-yl)-oxiranyl]-benzoic acid;

4-Benzoylamino-benzoic acid;

4-(3-tert-Butyl-benzoylamino)-benzoic acid;

4-(4-tert-Butyl-benzoylamino)-benzoic acid;

4-(3,5-Di-tert-butyl-benzoylamino)-benzoic acid;

4-(3,4-Diisopropyl-benzoylamino)-benzoic acid;

4-[(5,5,8,8-Tetramethyl-5,6,7,8-tetrahydro-naphthalene-2-carbonyl)-amino]-benzoic acid;

4-[Methyl-(5,5,8,8-tetramethyl-5,6,7,8-tetrahydro-naphthalene-2-carbonyl)-amino]-benzoic acid;
4-[(4,4-Dimethyl-chroman-7-carbonyl)-amino]-benzoic acid;
4-[(5-Chloro-4,4-dimethyl-chroman-7-carbonyl)-amino]-benzoic acid;
4-[(2,3-Dihydro-benzo[1,4]dioxine-6-carbonyl)-amino]-benzoic acid;
4-[(3,3-Dimethyl-3,4-dihydro-2H-benzo[b][1,4]-dioxepine-7-carbonyl)-amino]-benzoic acid;
4-[(5-Methyl-2,3,4,5-tetrahydro-benzo[b]thiepine-8-carbonyl)-amino]-benzoic acid;
4-[(4,4-Dimethyl-thiochroman-7-carbonyl)-amino]-benzoic acid;
4-[(Thiochroman-6-carbonyl)-amino]-benzoic acid;
4-[(2,3-Dihydro-benzo[1,4]dithiine-6-carbonyl)-amino]-benzoic acid;
4-[(4,4-Dimethyl-1,1-dioxo-1l>6_-thiochroman-7-carbonyl)-amino]-benzoic acid;
4-[(3-Methyl-1,1-dioxo-1l>6_-thiochroman-6-carbonyl)-amino]-benzoic acid;
4-[(1,4,4-Trimethyl-1,2,3,4-tetrahydro-quinoline-7-carbonyl)-amino]-benzoic acid;
4-[<1-Decyl-4,4-dimethyl-1,2,3,4-tetrahydro-quinoline-7-carbonyl)-amino]-benzoic acid;
4-(3-tert-Butyl-4-methoxy-benzoylamino)-benzoic acid;
4-(3-Adamantan-1-yl-4-hydroxy-benzoylamino)-benzoic acid;
4-(3-Adamantan-1-yl-4-methoxy-benzoylamino)-benzoic acid;
4-(3-Adamantan-1-yl-4-methoxy-benzoylamino)-2-hydroxy-benzoic acid;
4-(3-Adamantan-1-yl-4-hexyloxy-benzoylamino)-benzoic acid;
4-(3-Adamantan-1-yl-4-decyloxy-benzoylamino)-benzoic acid; IUPAC: 4-[3-(1,1-Dimethyl-decyl)-4-methoxy-benzoylamino]-benzoic; acid;
N-Phenyl-terephthalamic acid;
N-m-Tolyl-terephthalamic acid;
N-(3-Ethyl-phenyl)-terephthalamic acid;
N-(3-Isopropyl-phenyl)-terephthalamic acid;
N-(4-Isopropyl-phenyl)-terephthalamic acid;
N-(3-tert-Butyl-phenyl)-terephthalamic acid;
N-(4-tert-Butyl-phenyl)-terephthalamic acid;
N-(3-Cyclohexyl-phenyl)-terephthalamic acid;
N-Bi phenyl-3-yl-terephthalamic acid;
N-(3-Bromo-phenyl)-terephthalamic acid;
N-(3-Dimethylamino-phenyl)-terephthalamic acid;
N-(3-Trifluoromethyl-phenyl)-terephthalamic acid;
N-(3,4-Diethyl-phenyl)-terephthalamic acid;
N-(2-Isopropyl-phenyl)-terephthalamic acid;
N-(2,4-Diisopropyl-phenyl)-terephthalamic acid;
N-(2,5-Diisopropyl-phenyl)-terephthalamic acid;
N-(2,6-Diisopropyl-phenyl)-terephthalamic acid;
N-(3,4-Diisopropyl-phenyl)-terephthalamic acid;
N-(3,5-Diisopropyl-phenyl)-terephthalamic acid;
N-(2,4-Di-tert-butyl-phenyl)-terephthalamic acid;
N-(3,5-Di-tert-butyl-phenyl)-terephthalamic acid;
N-(3,4-Dichloro-phenyl)-terephthalamic acid;
N-(5,6,7,8-Tetrahydro-naphthalen-1-yl)-terephthalamic acid;
N-(5,6,7,8-Tetrahydro-naphthalen-2-yl)-terephthalamic acid;
N-(5,5,8,8-Tetramethyl-5,6,7,8-tetrahydro-naphthalen-1-yl)-terephthalamic acid;
N-(5,5,8,8-Tetramethyl-5,6,7,8-tetrahydro-naphthalen-2-yl)-terephthalamic acid;
N-(3,5,5,8,8-Pentamethyl-5,6,7,8-tetrahydro-naphthalen-2-yl)-terephthalamic acid;
N-Methyl-N-(5,5,8,8-tetramethyl-5,6,7,8-tetrahydro-naphthalen-2-yl)-terephthalamic acid;
N-Isopropyl-N-(5,5,8,8-tetramethyl-5,6,7,8-tetrahydro-naphthalen-2-yl)-terephthalamic acid;
N-(3-Bromo-5,5,8,8-tetramethyl-5,6,7,8-tetrahydro-naphthalen-2-yl)-terephthalamic acid;
3-Amino-5,5,8,8-tetramethyl-5,6,7,8-tetrahydro-naphthalen-2-yl)-terephthalamic acid;
N-(5,5,8,8-Tetramethyl-3-nitro-5,6,7,8-tetrahydro-naphthalen-2-yl)-terephthalamic acid;
N-(4,4-Dimethyl-chroman-6-yl)-terephthalamic acid;
N-(4,4-Dimethyl-thiochroman-6-yl)-terephthalamic acid;
Benzoic acid, 3,5-bis(1,1-dimethylethyl)-4-hydroxy-, carboxyphenyl ester;
Benzoic acid, 4-ethyl-3-(tricyclo[3.3.1.1$^{3,7}$]dec-1-yl)-, 4-carboxyphenyl ester;
Benzoic acid, 4-ethenyl-3-(tricyclo[3.3.1.1$^{3,7}$]dec-1-yl)-, 4-carboxyphenyl ester;
Benzoic acid, 4-methoxy-3-(tricyclo[3.3.1.1$^{3,7}$]dec-1-yl)-, 4-carboxyphenyl ester;
Benzoic acid, 4-methoxy-3-(tricyclo[3.3.1.1$^{3,7}$]dec-1-yl)-, 4-carboxy-3-methylphenyl ester;
Benzoic acid, 4-methoxy-3-(tricyclo[3.3.1.1$^{3,7}$]dec-1-yl)-, 4-carboxy-2-(hydroxymethyl)phenyl ester;
4-(4-Adamantan-1-yl-3-methoxy-benzoyloxy)-isophthalic acid;
Benzoic acid, 4-methoxy-3-(tricyclo[3.3.1.1$^{3,7}$]dec-1-yl)-, 4-carboxy-3-hydroxyphenyl ester;
Benzoic acid, 2,4-dimethoxy-5-(tricyclo-[3.3.1.1$^{3,7}$]dec1-yl)-, 4-carboxyphenyl ester;
Benzoic acid, 4-methoxy-3-(tricyclo[3.3.1.1$^{3,7}$]dec-1-yl)-, 4-carboxy-2-methoxyphenyl ester;
Benzoic acid, 4-methoxy-3-(tricyclo[3.3.1.1$^{3,7}$]dec-1-yl)-, 4-carboxy-3-methoxyphenyl ester;
Benzoic acid, 2-fluoro-4-methoxy-5-(tricyclo-[3.3.1.1$^{3,7}$]dec-1-yl)-, 4-carboxyphenyl ester;
Benzoic acid, 4-methoxy-3-(tricyclo[3.3.1.1$^{3,7}$]dec-1-yl)-, 4-carboxy-3-fluorophenyl ester;
Benzoic acid, 4-(2-propenyloxy)-3-(tricyclo-[3.3.1.1$^{3,7}$]dec-1-yl)-, 4-carboxyphenyl ester;
Benzoic acid, 4-(acetyloxy)-3-(tricyclo-[3.3.1.1$^{3,7}$]dec-1-yl)-, 4-carboxyphenyl ester;
Benzoic acid, 4-(2-methoxy-2-oxoethoxy)-3-(tricyclo[3.3.1.1$^{3,7}$]dec-1-yl)-, 4-carboxyphenyl ester;
Benzoic acid, 4-[2-(phenylmethoxy)-2-oxoethoxy]-3-(tricyclo-[ 3.3.1.1$^{3,7}$]dec-1-yl)-, 4-carboxyphenyl ester;
Benzoic acid, 4-(methylsulfonyl)-3-(tricyclo-[ 3.3.1.1$^{3,7}$]dec-1-yl)-, 4-carboxyphenyl ester;
4,4-Dimethyl-chroman-6-carboxylic acid 4-ethoxycarbonyl-phenyl ester;
2,2,4,4-Tetramethyl-chroman-6-carboxylic acid 4-ethoxycarbonyl-phenyl ester;

2,2,4,4,7-Pentamethyl-chroman-6-carboxylic acid 4-ethoxycarbonyl-phenyl ester;

4,4,7-Trimethyl-thiochroman-6-carboxylic acid 4-ethoxycarbonyl-phenyl ester;

2,2,4,4-Tetramethyl-thiochroman-6-carboxylic acid 4-ethoxycarbonyl-phenyl ester;

4-(5,5,8,8-Tetramethyl-5,6,7,8-tetrahydro-naphthalene-2-carbonylsulfanyl)-benzoic acid;

4-(3-Isopropyl-4-methoxy-benzoylsulfanyl)-benzoic acid;

4-(3-Isopropylsulfanyl-4-methyl-benzoylsulfanyl)-benzoic acid;

4-(3-Adamantan-1-yl-benzoylsulfanyl)-benzoic acid;

4-(5-Adamantan-1-yl-2-fluoro-4-methoxy-benzoylsulfanyl)-benzoic acid;

4-(5-Adamantan-1-yl-4-methoxy-2-methyl-benzoylsulfanyl)-benzoic acid;

4-(3-Adamantan-1-yl-4-allyloxy-benzoylsulfanyl)-benzoic acid;

4-(3-Adamantan-1-yl-4-methylsulfanyl-benzoylsulfanyl)-benzoic acid;

4-(3,5-Bis-trifluoromethyl-benzoylsulfanyl)-benzoic acid;

4-(4-tert-Butyl-benzylamino)-benzoic acid;

4-3,5-Di-tert-butyl-4-hydroxy-benzylamino)-benzoic acid;

4-4-tert-Butoxy-3-methoxy-benzylamino)-benzoic acid;

4-[4-(1-Methoxy-1-methyl-ethyl)-benzylamino]-benzoic acid;

4-[(5,5,8,8-Tetramethyl-5,6,7,8-tetrahydro-naphthalen-2-ylmethyl)-amino]-benzoic acid;

4-[(3-Fluoro-5,5,8,8-tetramethyl-5,6,7,8-tetrahydro-naphthalen-2-ylmethyl)-amino]-benzoic acid;

4-[(3-Methoxy-5,5,8,8-tetramethyl-5,6,7,8-tetrahydro-naphthalen-2-ylmethyl)-amino]-benzoic acid;

4-[(1,3-Dimethoxy-5,5,8,8-tetramethyl-5,6,7,8-tetrahydro-naphthalen-2-ylmethyl)-amino]-benzoic acid;

4-[(1-Butoxy-3,5,5,8,8-pentamethyl-5,6,7,8-tetrahydro-naphthalen-2-ylmethyl)-amino]-benzoic acid;

4-[(5,5,8,8-Tetramethyl-5,8-dihydro-naphthalen-2-ylmethyl)-amino]-benzoic acid;

4-[(5,5,8,8-Tetramethyl-7-oxo-5,6,7,8-tetrahydro-naphthalen-2-ylmethyl)-amino]-benzoic acid;

4-[(7-Hydroxy-5,5,8,8-tetramethyl-5,6,7,8-tetrahydro-naphthalen-2-ylmethyl)-amino]-benzoic acid;

4-[1-(7-Hydroxy-5,5,8,8-tetramethyl-5,6,7,8-tetrahydro-naphthalen-2-yl)-ethylamino]-benzoic acid;

4-[Methyl-(5,5,8,8-tetramethyl-5,6,7,8-tetrahydro-naphthalen-2-ylmethyl)-amino]-benzoic acid;

4-[Acetyl-(5,5,8,8-tetramethyl-5,6,7,8-tetrahydro-naphthalen-2-ylmethyl)-amino]-benzoic acid;

4-[(5-tert-Butyl-2-methyl-phenylamino)-methyl]-benzoic acid;

4-[(3,5-Di-tert-butyl-phenylamino)-methyl]-benzoic acid;

4-[(4-tert-Butyl-2,6-dimethyl-phenylamino)-methyl]-benzoic acid;

4-[(1,1,2,3,3-Pentamethyl-indan-5-ylamino)-methyl]-benzoic acid;

4-[1-(5,5,8,8-Tetramethyl-5,6,7,8-tetrahydro-naphthalet-2-ylamino)-ethyl]-benzoic acid;

4-[(1,4-Dichloro-5,5,8,8-tetramethyl-5,6,7,8-tetrahydro-naphthalen-2-ylamino)-methyl]-benzoic acid;

4-[(1,4-Dimethoxy-5,5,8,8-tetramethyl-5,6,7,8-tetrahydro-naphthalen-2-ylamino)-methyl]-benzoic acid;

4-{[Acetyl-(1,4-dimethoxy-5,5,8,8-tetramethyl-5,6,7,8-tetrahydro-naphthalen- 2-yl)-amino]-methyl}benzoic acid;

4-(4-tert-Butyl-phenoxymethyl)-benzoic acid;

4-(3-tert-Butyl-phenoxymethyl)-benzoic acid;

4-[4-(1,1-Dimethyl-propyl)-phenoxymethyl]-benzoic acid;

4-(2-tert-Butyl-4-methyl-phenoxymethyl)-benzoic acid;

4-(4-tert-Butyl-2-methyl-phenoxymethyl)-benzoic acid;

4-(2,4-Di-tert-butyl-phenoxymethyl)-benzoic acid;

4-(2,6-Di-tert-butyl-phenoxymethyl)-benzoic acid;

4-(2,5-Di-tert-butyl-phenoxymethyl)-benzoic acid;

4-(3,5-Di-tert-butyl-phenoxymethyl)-benzoic acid;

4-(2-sec-Butyl-4-tert-butyl-phenoxymethyl)-benzoic acid;

4-(2,4-Di-tert-butyl-5-methyl-phenoxymethyl)-benzoic acid;

4-(2,4,6-Tri-tert-butyl-phenoxymethyl)-benzoic acid;

4-(3,5-Di-tert-butyl-2-hydroxy-phenoxymethyl)-benzoic acid;

4-(5,5,8,8-Tetramethyl-3-nitro-5,6,7,8-tetrahydro-naphthalen-2-yloxymethyl)-benzoic acid;

4-(1,4-Dihydroxy-5,5,8,8-tetramethyl-5,6,7,8-tetrahydro-naphthalen-2-yloxymethyl)-benzoic acid;

4-(1,4-Diacetoxy-5,5,8,8-tetramethyl-5,6,7,8-tetrahydro-naphthalen-2-yloxymethyl)-benzoic acid;

4-i2,2,5,7,8-Pentamethyl-chroman-6-yloxymethyl)-benzoic acid;

4-[2-(2-Hydroxy-ethyl)-2,5,7,8-tetramethyl-chroman-6-yloxymethyl]-benzoic acid;

4-[2-(2-Acetoxy-ethyl)-2,5,7,8-tetramethyl-chroman-6-yloxymethyl]-benzoic acid;

4-(4-tert-Butyl-phenylsulfanylmethyl)-benzoic acid;

4-(4-tert-Butyl-2-methyl-phenylsulfanylmethyl)-benzoic acid;

4-(4-tert-Butyl-2-methyl-phenylsulfanylmethyl)-benzoic acid;

4-(4-tert-Butyl-2-methyl-phenylsulfanylmethyl)-benzoic acid;

4-(4-tert-Butyl-2-methyl-phenylsulfanylmethyl)-benzoic acid;

4-(4-tert-Butyl-2-methyl-phenylsulfanylmethyl)-benzoic acid;

4-(3,4-Diethyl-phenylazo)-benzoic acid;

4-(2-Isopropyl-phenylazo)-benzoic acid;

4-(3-Isopropyl-phenylazo)-benzoic acid;

4-(4-Isopropyl-phenylazo)-benzoic acid;

4-(2,4-Diisopropyl-phenylazo)-benzoic acid;

4-(2,6-Diisopropyl-phenylazo)-benzoic acid;

4-(3,4-Diisopropyl-phenylazo)-benzoic acid;

4-(3,5-Diisopropyl-phenylazo)-benzoic acid;

4-(3-tert-Butyl-phenylazo)-benzoic acid;

4-(3-Cyclohexyl-phenylazo)-benzoic acid;

4-(Biphenyl-3-ylazo)-benzoic acid;

4-(4,4-Dimethyl-thiochroman-6-ylazo)-benzoic acid;

4-[2-Hydroxy-2-(5,5,8,8-tetramethyl-5,6,7,8-tetrahydro-naphthalen-2-yl)-ethylamino]-benzoic acid;

4-[2-Hydroxy-2-(5,5,8,8-tetramethyl-5,6,7,8-tetrahydro-naphthalen- 2-yl)-ethylsulfanyl]-benzoic acid;

4-[2-Hydroxy-2-(5,5,8,8-tetramethyl-5,6,7,8-tetrahydro-naphthalen-2-yl)-ethoxy]-benzoic acid;

4-[N'-(5,5,8,8-Tetramethyl-5,6,7,8-tetrahydro-naphthalen-2-ylmethylene)-hydrazino]-benzoic acid;

4-{N'-[Cyclopropyl-(1,1,2,3,3-pentamethyl-indan-5-yl)-methylene]-hydrazino}-benzoic acid;

3,7-Dimethyl-9-(2,6,6-trimethyl-cyclohex-1-enyl)-nona-2,4,6,8-tetraenoic acid 2-{2-[2-(2-hydroxy-ethoxy)-ethoxy]-ethoxy}-ethyl ester;

3,7-Dimethyl-9-(2,6,6-trimethyl-cyclohex-1-enyl)-nona-2,4,6,8-tetraenoic acid 2-{2-[2-(2-hydroxy-ethoxy)-ethoxy]-ethoxy}-ethyl ester;

3,7-Dimethyl-9-(2,6,6-trimethyl-cyclohex-1-enyl)-nona-2,4,6,8-tetraenoic acid 2-(2-oxo-pyrrolidin-1-yl)-ethyl ester;

3,7-Dimethyl-9-(2,6,6-trimethyl-cyclohex-1-enyl)-nona-2,4,6,8-tetraenoic acid 2-(2-oxo-pyrrolidin-1-yl)-ethyl ester;

9-(4-Methoxy-2,3,6-trimethyl-phenyl)-3,7-dimethyl-nona-2,4,6,8-tetraenoic acid 2-{2-[2-(2-hydroxy-ethoxy)-ethoxy]-ethoxy}-ethyl ester;

9-(4-Methoxy-2,3,6-trimethyl-phenyl)-3,7-dimethyl-nona-2,4,6,8-tetraenoic acid 2-piperidin-1-yl-ethyl ester;

9-(4-Methoxy-2,3,6-trimethyl-phenyl)-3,7-dimethyl-nona-2,4,6,8-tetraenoic acid 2-morpholin-4-yl-ethyl ester;

9-(4-Methoxy-2,3,6-trimethyl-phenyl)-3,7-dimethyl-nona-2,4,6,8-tetraenoic acid 2-piperidin-1-yl-ethyl ester;

9-(4-Methoxy-2,3,6-trimethyl-phenyl)-3,7-dimethyl-nona-2,4,6,8-tetraenoic acid 2-(2,5-dioxo-pyrrolidin-1-yl)-ethyl ester;

9-{4-Methoxy-2,3,6-trimethyl-phenyl)-3,7-dimethyl-nona-2,4,6,8-tetraenoic acid 2-(2,6-dioxo-cyclohexyl)-ethyl ester;

9-(4-Methoxy-2,3,6-trimethyl-phenyl)-3,7-dimethyl-nona-2,4,6,8-tetraenoic acid 2-methanesulfonyl-ethyl ester;

9-(4-Methoxy-2,3,6-trimethyl-phenyl)-3,7-dimethyl-nona-2,4,6,8-tetraenoic acid methoxycarbonylmethyl ester;

9-(4-Methoxy-2,3,6-trimethyl-phenyl)-3,7-dimethyl-nona-2,4,6,8-tetraenoic acid tert-butoxycarbonylmethyl ester;

9-(4-Methoxy-2,3,6-trimethyl-phenyl)-3,7-dimethyl-nona-2,4,6,8-tetraenoic acid phenoxycarbonylmethyl ester;

9-(4-Methoxy-2,3,6-trimethyl-phenyl)-3,7-dimethyl-nona-2,4,6,8-tetraenoic acid 2-acetoxy-phenoxylcarbonylmethyl ester;

9-(4-Methoxy-2,3,6-trimethyl-phenyl)-3,7-dimethyl-nona-2,4,6,8-tetraenoic acid styryloxycarbonylmethyl ester;

9-(4-Methoxy-2,3,6-trimethyl-phenyl)-3,7-dimethyl-nona-2,4,6,8-tetraenoic acid 2-(4-methoxy-phenyl)vinyloxycarbonylmethyl ester;

9-(4-Methoxy-2,3,6-trimethyl-phenyl)-3,7-dimethyl-nona-2,4,6,8-tetraenoic acid 2-(benzoyl-carbonyl)-5-methoxy-phenoxymethoxycarbonyl-methyl ester;

9-(4-Methoxy-2,3,6-trimethyl-phenyl)-3,7-dimethyl-nona-2,4,6,8-tetraenoic acid 1-phenoxycarbonyl-ethyl ester;

9-(4-Methoxy-2,3,6-trimethyl-phenyl)-3,7-dimethyl-nona-2,4,6,8-tetraenoic acid 1-ethoxycarbonyloxy-ethyl ester;

3,7-Dimethyl-9-(2,6,6-trimethyl-cyclohex-1-enyl)-nona-2,4,6,8-tetraenoic acid 2-butoxy-4-dimethylamino-6-methyl-tetrahydro-pyran-3-yl ester;

3,7-Dimethyl-9-(2,6,6-trimethyl-cyclohex-1-enyl)-nona-2,4,6,8-tetraenoic acid 2-butoxy-4-dimethylamino-6-methyl-tetrahydro-pyran-3-yl ester;

3,7-Dimethyl-9-(2,6,6-trimethyl-cyclohex-1-enyl)-nona-2,4,6,8-tetraenoic acid 2-butoxy-4-dimethylamino-6-methyl-tetrahydro-pyran-3-yl ester;

3,7-Dimethyl-9-(2,6,6-trimethyl-cyclohex-1-enyl)-nona-2,4,6,8-tetraenoic acid 4-dimethylamino-6-methyl-2-(2-octyl-hexadecyloxy)-tetrahydro-pyran-3-yl ester;

9-(4-Methoxy-2,5,6-trimethyl-cyclohex-1-enyl)-3,7-dimethyl-nona-2,4,6,8-tetraenoic acid 2-butoxy-4-dimethylamino-6-methyl-tetrahydro-pyran-3-yl ester;

9-(4-Methoxy-2,5,6-trimethyl-cyclohex-1-enyl)-3,7-dimethyl-nona-2,4,6,8-tetraenoic acid 2-butoxy-4-dimethylamino-6-methyl-tetrahydro-pyran-3-yl ester;

9-{4-Methoxy-2,5,6-trimethyl-cyclohex-1-enyl)-3,7-dimethyl-nona-2,4,6,8-tetraenoic acid 2-butoxy-4-dimethylamino-6-methyl-tetrahydro-pyran-3-yl ester;

4-[4-(2,6,6-Trimethyl-cyclohex-1-enyl)-but-3-en-1-ynyl]-benzamide;

3,7-Dimethyl-9-(2,6,6-trimethyl-cyclohex-1-enyl)-nona-2,4,6,8-tetraenoic acid aide;

[6-(3-Adamantan-1-yl-4-methoxy-phenyl)-naphthalen-2-yl]-morpholin-4-yl-methanone;

N-(3,5-Bis-trifluoromethyl-phenyl)-4-(5,5,8,8-tetramethyl-5,6,7,8-tetrahydro-naphthalene- 2-carbonyl)-benzamide;

N-(4-Hydroxy -phenyl)-4-[2-(5,5,8,8-tetramethyl-5,6,7, 8-tetrahydro-naphthalen-2-yl)-vinyl]-benzamide;

N-{3,5-Bis-trifluoromethyl-phenyl)-4-(5,5,8,8-tetramethyl-5,6,7,8-tetrahydro-naphthalene-2-carbonyl)-benzamide;

[3,7-Dimethyl-9-(2,6,6-trimethyl-cyclohex-1-enyl)-nona-2,4,6,8-tetraenoylamino]-acetic acid;

[3,7-Dimethyl-9-(2,6,6-trimethyl-cyclohex-1-enyl)-nona-2,4,6,8-tetraenoylamino]-acetic acid;

2-[3,7-Dimethyl-9-(2,6,6-trimethyl-cyclohex-1-enyl)-nona- 2,4,6,8-tetraenoylamino]-4-methyl-pentanoic acid;

2-[3,7-Dimethyl-9-(2,6,6-trimethyl-cyclohex-1-enyl)-nona- 2,4,6,8-tetraenoylamino]-3-phenyl-propionic acid;

2-[3,7-Dimethyl-9-(2,6,6-trimethyl-cyclohex-1-enyl)-nona- 2,4,6,8-tetraenoylamino]-3-(4-hydroxy-phenyl)-propionic acid;

2-[3,7-Dimethyl-9-(2,6,6-trimethyl-cyclohex-1-enyl)-nona-2,4,6,8-tetraenoylamino]-pentanedioic acid;

[3,7-Dimethyl-9-(2,6,6-trimethyl-cyclohex-1-enyl)-nona-2 ,4,6,8-tetraenoylamino]-acetic acid;

2-[3,7-Dimethyl-9-(2,6,6-trimethyl-cyclohex-1-enyl)-nona-2,4,6,8-tetraenoylamino]-propionic acid;

2-[3,7-Dimethyl-9-(2,6,6-trimethyl-cyclohex-1-enyl)-nona-2,4,6,8-tetraenoylamino]- 4-methyl-pentanoic acid;

2-[3,7-Dimethyl-9-(2,6,6-trimethyl-cyclohex-1-enyl)-nona-2,4,6,8-tetraenoylamino]- 3-phenyl-propionic acid;

4-[3,7-Dimethyl-9-(3,3,6,6-tetramethyl-cyclohex-1-enyl)-nona-2,4,6-trien- 8-ynoylamino]-benzoic acid;

2-[3,7-Dimethyl-9-(2,6,6-trimethyl-cyclohex-1-enyl)-nona- 2,4,6,8-tetraenoyl]-benzo[d]isothiazol-3-one;

4-[2-(8,8-Dimethyl-5,6,7,8-tetrahydro-naphthalen-2-yl)-propenyl]-N-(1H-tetrazol- 5-yl)-benzamide;

[3,7-Dimethyl-9-(2,6,6-trimethyl-cyclohex-1-enyl)-nona-2,4,6,S-tetraenoylamino]-acetic acid;

4-Methyl-7-(5,5,8,8-tetramethyl-5,6,7,8-tetrahydro-naphthalen-2-yl)-octa-2,4,6-trienoic acid ethylamide;

{4-[4-(2-Hydroxy-ethyl)-piperazine-1-carbonyl]-phenyl}-(5,5,8,8-tetramethyl- 5,6,7,8-tetrahydro-naphthalen-2-yl)-methanone;

6-(5,5,8,8-Tetramethyl-5,6,7,8-tetrahydro-naphthalene-2-carbonyl)-naphthalene-2-carboxylic acid [(2-hydroxy-ethoxy)-ethyl]-amide;

6-(5,5,8,8-Tetramethyl-5,6,7,8-tetrahydro-naphthalene-2-carbonyl)-naphthalene-2-carboxylic acid (4-hydroxy-phenyl)-amide;

4-Methylsulfanyl-2-{[6-(5,5,8,8-tetramethyl- 5,6,7,8-tetrahydro-naphthalene-2-carbonyl)-naphthalene-2-carbonyl]-amino}-butyric acid;

5-(4-Adamantan-2-ylidenemethyl-phenyl)-3-methyl-penta-2,4-dienoic acid (2-ethyl-hexyl)-amide;

2-[5-(4-Adamantan-2-ylidenemethyl-phenyl)-3-methyl-penta-2,4-dienoylamino]- 4-methylsulfanyl-butyric acid ethyl ester;

4-[2-(1,3-Dimethoxy-5,5,8,8-tetramethyl-5,6,7,8-tetrahydro-naphthalen-2-yl)-vinyl]-N-(2-hydroxy-ethyl)-benzamide;

N-Butyl-2-(5,5,8,8-tetramethyl-5,6,7,8-tetrahydro-naphthalene-2-carbonyl)-benzamide; N-(2-Hydroxy-ethyl)-2-(5,5,8,8-tetramethyl-5,6,7,8-tetrahydro-naphthalene-2-carbonyl)-benzamide;

{2-[4-(2-Hydroxy-ethyl)-piperazine-1-carbonyl-carbonyl]-phenyl}-( 5,5,8,8-tetramethyl-5,6,7,8-tetrahydro-naphthalen-2-yl)-methanone;

3-Adamantan-1-yl-4-methoxy-benzoyl chloride;

4-Amino-N-tert-butyl-benzamide;

4-Amino-N-phenyl-benzamide;

4-Amino-N-benzyl-benzamide;

4-Amino-N-(2-hydroxy-ethyl)-benzamide;

(4-Amino-phenyl)-pyrrolidin-1-yl-methanone;

(4-Amino -phenyl)-piperidin -1-yl-methanone;

(4-Amino -phenyl)-morpholin -4-yl-methanone;

Benzamide, N-[4-[[(1,1-dimethylethyl) amino]-carbonyl] phenyl]- 4-methoxy-3-(tricyclo[3.3.1.13, 7]dec-1-yl)-;

Benzamide, N-[4-[(phenylamino)carbonyl]-phenyl]-4-methoxy- 3-(tricyclo[3.3.1.1$^{3,7}$]dec-1-yl)-;

Benzamide, N-[4-[[(phenylmethyl)amino]carbonyl]-phenyl]-4-methoxy- 3-(tricyclo[3.3.1.1$^{3,7}$]dec-1-yl)-;

Benzamide, N-[4-[[(2-hydroxyethyl)amino]carbonyl]-phenyl]-4-methoxy- 3-(tricyclo[3.3.1.1$^{3,7}$]dec-1-yl)-;

-Adamantan-1-yl-4-methoxy-N-[4-(pyrrolidine-1-carbonyl-carbonyl)-phenyl]-benzamide;

3-Adamantan-1-yl-4-methoxy-N-[4-(piperidine-1-carbonyl-carbonyl)-phenyl]-benzamide;

3-Adamantan-1-yl-4-methoxy-N-[4-(morpholine-4-carbonyl-carbonyl)-phenyl]-benzamide;

1,1,3,3-Tetramethyl-5-(1-methyl-2-phenyl-vinyl)-indan;

6-(1-Methyl-2-phenyl-vinyl)-1,2,3,4-tetrahydro-naphthalene;

6-(1-Methyl-2-phenyl-vinyl)-1,2,3,4-tetrahydro-naphthalene;

1,1-Dimethyl-6-(1-methyl-2-phenyl-vinyl)-1,2,3,4-tetrahydro-naphthalene;

1,1,4,4-Tetramethyl-6-(1-methyl-2-phenyl-vinyl)-1,2,3, 4-tetrahydro-naphthalene;

1,1,4,4,6-Pentamethyl-7-(1-methyl-2-phenyl-vinyl)-1,2, 3,4-tetrahydro-naphthalene;

1,1,4,4-Tetramethyl-6-(1-methyl-2-phenyl-vinyl)-7-octyl-1,2,3,4-tetrahydro-naphthalene;

6-Methoxy-1,1,4,4-tetramethyl-7-(1-methyl-2-phenyl-vinyl)-1,2,3,4-tetrahydro-naphthalene;

6-Chloro-1,1,4,4-tetramethyl-7-(1-methyl-2-phenyl-vinyl)-1,2,3,4-tetrahydro-naphthalene;

(Z)-1,1,4,4-Tetramethyl-6-(1-methyl-2-phenyl-vinyl)-1, 2,3,4-tetrahydro-naphthalene;

1,1,4,4-Tetramethyl-6-(1-methyl-2-phenyl-vinyl)-1,2,3, 4-tetrahydro-naphthalen-2-ol;

1,1,4,4,6-Pentamethyl-7-(1-methyl-2-phenyl-vinyl)-1,2, 3,4-tetrahydro-naphthalen-2-ol;

1,1,3,3-Tetramethyl-5-(1-methyl-2-phenyl-vinyl)-indan-2-one;

1,4,4-Trimethyl-7-(1-methyl-2-phenyl-vinyl)-1,2,3,4-tetrahydro-quinoline;

1.4,4-Trimethyl-6-(1-methyl-2-phenyl-vinyl)-1,2,3,4-tetrahydro-quinoline;

4,4-Dimethyl-7-(1-methyl-2-phenyl-vinyl)-chroman;

4,4-Dimethyl-6-(1-methyl-2-phenyl-vinyl)-chroman;

450) IUPAC: 4,4-Dimethyl-7-(1-methyl-2-phenyl-vinyl)-thiochroman;

4,4-Dimethyl-6-(1-methyl-2-phenyl-vinyl)-thiochroman;

4,4-Dimethyl-7-(1-methyl-2-phenyl-vinyl)-thiochroman 1,1-dioxide;

4,4-Dimethyl-6-(1-methyl-2-phenyl-vinyl)-thiochroman 1,1-dioxide;

2,2-Dimethyl-5-(1-methyl-2-phenyl-vinyl)-benzo[1,3] dithiole;

7,7-Dimethyl-2-(1-methyl-2-phenyl-vinyl)-7,8-dihydro-6H-5,9-dithia-benzocycloheptene;

1,1,3,3-Tetramethyl-indan-5-carboxylic acid phenylamide;

5,5,8,8-Tetramethyl-5,6,7,8-tetrahydro-naphthalene-2-carboxylic acid phenylamide;

5,5,7,7,9,9-Hexamethyl-6,7,8,9-tetrahydro-H-benzocycloheptene-2-carboxylic acid phenylamide;

459) IUPAC: N-(1,1,3,3-Tetramethyl-indan-5-yl)-benzamide;

N-(5,5,8,8-Tetramethyl-5,6,7,8-tetrahydro-naphthalen-2-yl)-benzamide;

3-Adamantan-1-yl-4-methoxy-benzoic acid phenyl ester;

3-Adamantan-1-yl-4-methoxy-thiobenzoic acid S-phenyl ester;

4-[2-(5,5,8,8-Tetramethyl-5,6,7,8-tetrahydro-naphthalen-2-yl)-propenyl]-phenol;

Acetic acid 4-[2-(5,5,8,8-tetramethyl-5,6,7,8-tetrahydro-naphthalen-2-yl)-propenyl]-phenyl ester;

1-(2-{4-[2-(5,5,8,8-Tetramethyl-5,6,7,8-tetrahydro-naphthalen- 2-yl)-propenyl]-phenoxy }-ethyl)-piperidine;

4-(2-{4-[2-(5,5,8,8-Tetramethyl-5,6,7,8-tetrahydro-naphthalen- 2-yl)-propenyl]-phenoxy}-ethyl)-morpholine;

4-(2-{4-[2-(5,5,8,8-Tetramethyl-5,6,7,8-tetrahydro-naphthalen- 2-yl)-propenyl]-phenoxy}-ethyl)-thiomorpholine 1,1-dioxide;

4-[2-(3-Chloro-5,5,8,8-tetramethyl-6,7,8-tetrahydro-naphthalen-2-yl)-propenyl]-phenol;

4-[2-(6-Methoxy-1,1,3,3-tetramethyl-indan-5-yl)-propenyl]-phenol;

5-[2-(4-Hydroxy-phenyl)-1-methyl-vinyl]-1,1,3,3-tetramethyl-indan-2-one;

5,5,8,8-Tetramethyl-5,6,7,8-tetrahydro-naphthalene-2-2-carboxylic acid (4-hydroxy-phenyl)-amide; 7,7-Dimethyl-6,7,8,9-tetrahydro-5H-benzocyclo-heptene-2-carboxylic acid (4-hydroxy-phenyl)-amide;

3-Ethyl-7,7-dimethyl-6,7,8,9-tetrahydro-5H-benzocycloheptene-2-carboxylic acid (4-hydroxy-phenyl) amide;

4-Hydroxy-N-(5,5,8,8-tetramethyl-5,6,7,8-tetrahydro-naphthalen-2-yl)-benzamide;

3-Adamantan-1-yl-4-methoxy-benzoic acid 4-hydroxyphenyl ester;

3-Adamantan-1-yl-4-methoxy-thiobenzoic acid S-(4-hydroxy-phenyl) ester;

5-[2-Methyl-4-(2,6,6-trimethyl-cyclohex-1-enyl)-buta-1,3-dienyl]-1H-tetrazole;

5-{4-[2-(5,5,8,8-Tetramethyl-5,6,7,8-tetrahydro-naphthalen- 2-yl)-propenyl]-phenyl}-1H-tetrazole;

5-[4-(5,5,8,8-Tetramethyl-5,6,7,8-tetrahydro-naphthalen-2-ylethynyl)-phenyl]-1H-tetrazole;

Methyl-{4-[2-(5,5,8,8-tetramethyl-5,6,7,8-tetrahydro-naphthalen- 2-yl)-propenyl]-phenyl}-phosphinic acid ethyl ester;

Phenyl-{4-[2-(5,5,8,8-tetramethyl-5,6,7,8-tetrahydro-naphthalen- 2-yl)-propenyl]-phenyl}-phosphinic acid ethyl ester;

{4-[2-(5,5,8,8-Tetramethyl-5,6,7,8-tetrahydro-naphthalen-2-yl)-propenyl]-phenyl}-phosphonic acid dimethyl ester;

{4-[2-(5,5,8,8-Tetramethyl-5,6,7,8-tetrahydro-naphthalen-2-yl)-propenyl]-phenyl}-phosphonic acid diethyl ester;

{4-[2-(5,5,8,8-Tetramethyl-5,6,7,8-tetrahydro-naphthalen-2-yl)-propenyl]-phenyl}-phosphonic acid dibutyl ester;

{4-[2-(1,1,2,3,3-Pentamethyl-indan-5-yl)-propenyl]-phenyl}-phosphonic acid diethyl ester;

6-(2-Biphenyl-4-yl-1-methyl-vinyl)-1,1,4,4-tetramethyl-1,2,3,4-tetrahydro-naphthalene;

6-[2-(2-Fluoro-phenyl)-1-methyl-vinyl]-1,1,4,4-tetramethyl-1,2,3,4-tetrahydro-naphthalene;

6-[2-(2-Fluoro-phenyl)-1-methyl-vinyl]-1,1,4,4-tetramethyl-1,2,3,4-tetrahydro-naphthalene;

6-[2-(4-Chloro-phenyl)-1-methyl-vinyl]-1,1,4,4-tetramethyl-1,2,3,4-tetrahydro-naphthalene;

6-[2-(2-Bromo-phenyl)-1-methyl-vinyl]-1,1,4,4-tetramethyl-1,2,3,4-tetrahydro-naphthalene;

6-[2-(3-Bromo-phenyl)-1-methyl-vinyl]-1,1,4,4-tetramethyl-1,2,3,4-tetrahydro-naphthalene;

6-[2-(4-Iodo-phenyl)-1-methyl-vinyl]-1,1,4,4-tetramethyl-1,2,3,4-tetrahydro-naphthalene;

1,1,4,4-Tetramethyl-6-[1-methyl-2-(4-nitrophenyl)-vinyl]-1,2,3,4-tetrahydro-naphthalene;

1,1,3,3-Tetramethyl-indan-5-carboxylic acid (4-fluoro-phenyl)-amide;

5,5,8,8-Tetramethyl-5,6,7,8-tetrahydro-naphthalene-2-carboxylic acid (4-fluoro-phenyl)-amide;

9,9-Dimethyl-6,7,8,9-tetrahydro-5H-benzocycloheptene-2-carboxylic acid (4-fluoro-phenyl)-amide;

7,7-Dimethyl-6,7,8,9-tetrahydro-5H-benzocycloheptene-2-carboxylic acid (4-fluoro-phenyl)-amide;

4-Fluoro-N-(1,1,3,3-tetramethyl-indan-5-yl)-benzamide;

4-Fluoro-N-(5,5,8,8-tetramethyl-5,6,7,8-tetrahydro-naphthalen-2-yl)-benzamide;

$N^1,N^1$-Dimethyl-$N^2$-{4-[2-(5,5,8,8-tetramethyl-5,6,7,8-tetrahydro-naphthalen-2-yl)-propenyl]-phenyl}-ethane-1,2-diamine;

Methyl-(2-morpholin-4-yl-ethyl)-{4-[2-(5,5,8,8-tetramethyl-5,6,7,8-tetrahydro-naphthalen-2-yl)-propenyl]-phenyl}-amine;

6-{2-[4-(2-Methoxy-ethylsulfanyl)-phenyl]-1-methyl-vinyl}-1,1,4,4-tetramethyl-1,2,3,4-tetrahydro-naphthalene; and 1,1,4,4-Tetramethyl-6-{1-methyl-2-[4-(2-methylsulfanyl-ethylsulfanyl)-phenyl]-vinyl}-1,2,3,4-tetrahydro-naphthalene.

As can be seen from the foregoing, this invention contemplates the use of any compound which falls within the generic term "retinoids". All that is required to lower plasma levels of Lp(a) according to this invention is to administer to an animal an Lp(a) lowering amount of a retinoid. All of the retinoids to be utilized are either known or are readily prepared as described by Dawson and Hobbs, ibid., which is incorporated herein by reference.

We have evaluated several specific retinoids for their ability to lower Lp(a) levels in animals. The compounds were evaluated according to the following protocol.

Hepatocytes were isolated from male monkeys (Cynomolgus macaca) of approximately 6.5 kg as described by Ulrich R. G., Aspar D. G., Cramer C. T., Kletzien R. F., Ginsberg L. C., *In Vitro Cell Dev. Biol.* 1990;26:815–23, except that the final cell suspension was purified by Percoll density gradient centrifugation. The resulting cell pellet, containing the viable hepatocytes, was washed, counted, and resuspended in fetal bovine serum (FBS), 90%, and DMSO, 10%, at a concentration of $10^6$ cells/mL. Cells were frozen in the FBS/DMSO medium at a rate of 1/minute using a controlled-rate liquid nitrogen freezer and stored in a liquid nitrogen freezer. Only previously frozen cells were used. Frozen cells were thawed in a 37° C. water bath, pelleted by centrifugation, resuspended in Dulbecco's modified eagle medium (DMEM) containing FBS, 10%, and plated at a concentration $3\times10^6$ cells/60-mm plate. The medium was changed 4 hours later. The next day (Day 0) the medium was replaced with fresh medium not containing FBS and a further 24-hour incubation was carried out. All subsequent incubations were performed in the absence of FBS, however, the culture medium was supplemented with 0.2% bovine serum albumin (BSA). On Day 1 fresh medium was added to the cells. The following day (Day 2) drug treatment was initiated by incubating the cells for 24 hours with the test compounds or the appropriate concentration of the DMSO vehicle (0.3%–0.5%). Triplicate wells were used for each retinol or DMSO dose. Every 24 hours for the next 2 days (Days 2 and 3) fresh medium containing the test compounds or DMSO was added to the cells. On Day 5 the medium was collected, frozen at −70° C., and within 1 week analyzed for Lp(a) levels using a specific Lp(a) ELISA. The data is presented in Table 1 and is expressed as percent inhibition at a single concentration, relative Lo cells treated with vehicle only.

TABLE I

| Compound at 10 µM | Percent Lowering of LP(a) |
| --- | --- |
| All trans-Retinoic acid | 80 |
| All trans-Retinoic acid, methyl ester | 37 |
| All trans-Retinal | 80 |
| All trans-Retinol | 77 |
| 9-cis-retinoic acid | 42 |
| 13-cis-retinol | 59 |
| 13-cis-retinal | 66 |
| 9-cis-retinal | 76 |
| 3-methyl-5-(2,6,6-trimethyl-1-cyclohexan-1-yl)-2,4-pentadienoic acid | 34 |
| 3-methyl-5-(2,6,6-trimethyl-1-cyclohexan-1-yl)-2,4-pentadienoic acid, methyl ester | 68 |
| 3-methyl-5-(2,6,6-trimethyl-1-cyclohexen-1-yl)-2,4-pentadienoic acid, ethyl ester | 46 |
| 3-methyl-5-(2,6,6-trimethyl-1-cyclohexen-1-yl)-2,4-pentadien-1-ol | 50 |
| 3-methyl-5-(2,6,6-trimethyl)-1-cyclohexen-1-yl)-2,4-pentadienal | 72 |
| 3-methyl-5-(2,6,6-trimethyl-1-cyclohexen-1-yl)-pentanoic acid | 28 |
| 5,5,6-trimethyl-3-cyclohexen-1-carboxaldehyde | 20 |

For use in the method of this invention, the retinoids preferably are combined with one or more pharmaceutically acceptable diluents, carriers, excipients, or the like, for convenient oral, parenteral, and topical administration to animals, preferably humans. The retinoids are ideally suited to formulation for oral administration in the form of tablets, capsules, dispersible powders, granules, suspensions, elixirs, buccal seals, and the like. The formulations typically will contain from about 1% to about 90% by weight of active retinoid, and more commonly from about 5% to about 60% by weight.

Oral formulations can contain, for suspensions, from about 0.05% to about 5% by weight of a suspending agent, such as talc or the like, and syrups will contain from about 10% to about 50% by weight of a sugar such as dextrose. Tablets may contain normal amounts of binders, stabilizers, and common diluents i0 such as corn starch and sugars. Parenteral formulations, for instance, solutions for IV injection, will be made by dissolving or suspending the retinoid in a solvent such as isotonic saline or 5% glucose in sterile water.

The dose of retinoid to be administered is that amount which is effective for lowering plasma levels of Lp(a) in an animal.

The effective dosage of active ingredient employed may vary depending on the particular compound employed, the mode of administration, and the severity of the condition being treated. However, in general, satisfactory results are obtained when the retinoids are administered at a daily dosage of from about 0.5 to about 500 mg/kg of animal body weight, preferably given in divided doses two to four times a day, or in sustained-release form. For most large mammals, such as humans, the total daily dosage is form about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The retinoids may be administered orally as well as by intravenous, intramuscular, or subcutaneous routes. Solid carriers include starch, lactose, dicalcium phosphate, microcrystalline cellulose, sucrose, and kaolin, while liquid carriers include sterile water, polyethylene glycols, nonionic surfactants, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT, and BHA.

The preferred pharmaceutical compositions from the stand point of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (eg, glycerol, propylene glycol, and liquid polyethylene glycol), suitable mixtures thereof, and vegetable oils.

The compounds may also be encapsulated in liposomes to allow an intravenous administration of the drug. The liposomes suitable for use in the invention are lipid vesicles and may include plurilamellar lipid vesicles, small sonicated multimellar vesicles, reverse phase evaporation vesicles, large multilamellular vesicles, and the like, wherein the lipid vesicles are formed by one or more phospholipids such as phosphotidylcholine, phosphatidylglycerol, sphingomyelin, phospholactic acid, and the like. In addition, the liposomes may also comprise a sterol component such as cholesterol.

Some typical formulations which can be administered to humans are as follows:

Tablet Formulation

4-[2-(3,4-di-n-butylphenyl)-propenyl]-benzoic acid (250 mg) is blended to uniformity with 100 mg of corn starch and 50 mg of lactose. The mixture is compressed into a tablet. Such tablets are administered orally at the rate of one to three times a day.

| Preparation of Oral Suspension | |
| --- | --- |
| Ingredient | Amount |
| 4,4-dimethyl-7-(1-methyl-2-phenylvinyl)chroman | 500 mg |
| Sorbitol solution (70% NF) | 40 mL |
| Sodium benzoate | 150 mg |
| Saccharin | 10 mg |
| Red dye | 10 mg |
| Cherry flavor | 50 mg |
| Distilled water qs OD | 100 mL |

The sorbitol solution is added to 40 mL of distilled water and the retinoid is suspended thereon. The saccharin, sodium benzoate, flavor, and dye are added and dissolved. The volume is adjusted to 100 mL with distilled water. Each milliliter of syrup contains 5 mg of retinoid.

Suppositories

A mixture of 400 mg of 4-(2,4-diisopropylbenzoyl)-benzoic acid and 600 mg of theobroma oil is stirred at 60° C. to uniformity. The mixture is cooled and allowed to harden in a tapered mold to provide a 1-g suppository.

Parenteral Solution

In a solution of 700 mL of propylene glycol and 200 mL of sterile water is suspended 20.0 g of retinoic acid. The pH is adjusted to pH 6.5 with dilute sodium hydroxide, and the volume is made up to 100 mL with water for injection. The formulation is sterilized, filled into 5.0-mL ampoules each containing 2.0 mL (representing 40 mg of drug), and sealed under nitrogen.

Preferred formulations are those incorporating any of the preferred retinoids to be utilized to lower Lp(a). Specifically preferred are all trans isomers of retinoic acid, retinal, and retinol. Also preferred are the 9-cis isomers of retinoic acid, retinal, and retinol, as well as the 13-cis isomers of retinoic acid, retinal, and retinol. Certain retinoid esters also are preferred, for example, 3,7-dimethyl-9-(2,6,6-trimethyl-cyclohex-1-enyl)-nona-2,4,6,8-tetraenoic acid, methyl ester.

We claim:

1. A method of lowering plasma Lp(a) levels in a mammal comprising administering an Lp(a) lowering amount of a retinoid.
2. A method of claim 1 employing all trans-retinoic acid.
3. A method of claim 1 employing 3,7-dimethyl-9-(2,6,6-trimethyl-cyclohex-1-enyl)-nona-2,4,6,8-tetraenoic acid, methyl ester.
4. A method of claim 1 employing all trans-retinal.
5. A method of claim 1 employing all trans-retinol.
6. A method of claim 1 employing 9-cis-retinoic acid.
7. A method of claim 1 employing 13-cis-retinol.
8. A method of claim 1 employing 13-cis-retinal.
9. A method of claim 1 employing 9-cis-retinol.
10. A method of claim 1 employing 13-cis-retinoic acid.
11. A method of claim 1 employing 9-cis-retinal.

* * * * *